United States Patent [19]

Kanno et al.

[11] 4,413,006

[45] Nov. 1, 1983

[54] N-ARYL-N-PHENOXY-ALKYL-PIPERAZINE COMPOUNDS USEFUL IN DECREASING INTRACRANIAL PRESSURE

[75] Inventors: Takeshi Kanno; Mitsunori Gaino, both of Omiya; Michio Yamamura, Tondabayashi; Ryuichi Ishida; Keiichi Shintomi, both of Suita, all of Japan

[73] Assignee: Tanabe Seiyaku Co., Ltd., Osaka, Japan

[21] Appl. No.: 374,106

[22] Filed: May 3, 1982

Related U.S. Application Data

[62] Division of Ser. No. 231,094, Feb. 3, 1981, abandoned.

[30] Foreign Application Priority Data

Feb. 18, 1980 [JP] Japan .................................. 55-18855

[51] Int. Cl.$^3$ .................. C07D 295/00; A01N 43/48; A61K 31/495; C07D 403/00; C07D 241/04
[52] U.S. Cl. ..................................... 424/250; 544/372; 544/392; 549/419
[58] Field of Search ........................................ 424/250

[56] References Cited

U.S. PATENT DOCUMENTS 4,100,282 7/1978 Renth et al. ..................... 424/250

FOREIGN PATENT DOCUMENTS 997166 7/1965 United Kingdom ................ 544/392

*Primary Examiner*—Donald G. Daus
*Assistant Examiner*—S. A. Gibson
*Attorney, Agent, or Firm*—Jordan B. Bierman; Linda Bierman

[57] ABSTRACT

A piperazine derivative of the formula:

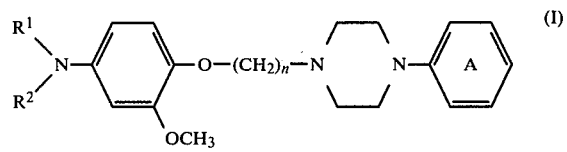

wherein $R^1$ is hydrogen, alkyl ($C_{1-8}$), alkyl ($C_{1-4}$)-sulfonyl or an acyl group of the formula: $R^3CO$—(wherein $R^3$ is hydrogen, alkyl ($C_{1-7}$), halogenoalkyl ($C_{1-4}$), alkoxy ($C_{1-4}$)-carbonyl-alkyl ($C_{1-4}$), cycloalkyl ($C_{3-6}$), alkenyl ($C_{2-5}$), alkoxy ($C_{1-4}$), amino, alkyl ($C_{1-4}$)-amino or anilino), $R^2$ is hydrogen, alkyl ($C_{1-4}$), alkoxy ($C_{1-4}$)-carbonyl-alkyl ($C_{1-4}$), carboxy-alkyl ($C_{1-4}$), alkenyl ($C_{2-5}$) or alkyl ($C_{1-4}$)-sulfonyl, or $R^1$ and $R^2$ are combined together to form succinyl group, Ring A is phenyl, alkyl ($C_{1-4}$)-phenyl or halogenophenyl, and n is an integer of 2 to 6, or a pharmaceutically acceptable acid addition salt thereof. The piperazine derivative (I) has an intracranial pressure-lowering activity. Said derivative also has a depressing effect on central nervous system.

19 Claims, No Drawings

N-ARYL-N-PHENOXY-ALKYL-PIPERAZINE COMPOUNDS USEFUL IN DECREASING INTRACRANIAL PRESSURE

The instant application is a divisional application of Ser. No. 231,094, filed Feb. 3, 1981, now abandoned, Dec. 22, 1981, which claims the priority of Japanese Application No. 18855/1980, filed Feb. 15, 1980.

This invention relates to a piperazine derivative and method for using the same. More particularly, it relates to a piperazine derivative of the formula:

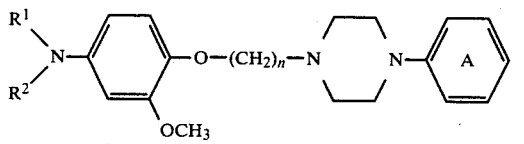

wherein $R^1$ is hydrogen, alkyl ($C_{1-8}$), alkyl ($C_{1-4}$)-sulfonyl or an acyl group of the formula: $R^3CO-$ (wherein $R^3$ is hydrogen, alkyl ($C_{1-7}$), halogenoalkyl ($C_{1-4}$), alkoxy ($C_{1-4}$)-carbon-alkyl ($C_{1-4}$), cycloalkyl ($C_{3-6}$), alkenyl ($C_{2-5}$), alkoxy ($C_{1-4}$), amino, alkyl ($C_{1-4}$)-amino or anilino), $R^2$ is hydrogen, alkyl ($C_{1-4}$), alkoxy ($C_{1-4}$)-carbonyl-alkyl ($C_{1-4}$), carboxy-alkyl ($C_{1-4}$), alkenyl ($C_{2-5}$) or alkyl ($C_{1-4}$)-sulfonyl, or $R^1$ and $R^2$ are combined together to form succinyl group, Ring A is phenyl, alkyl ($C_{1-4}$)-phenyl or haogenophenyl, and n is an integer of 2 to 6, or a pharmaceutically acceptable acid addition salt thereof.

Cerebral edema, which is a well-known comlication of various cerebral diseases (e.g., cerebral hemorrhage, subarachnoid hemorrhage, cerebral thrombosis, cerebral embolism, head injury, cerebral tumor and encephalomyelitis), induces an increase in intracranial pressure due to compression of neighbouring brain tissues. Moreover, such increased intracranial pressure is known to adversely affect cerebral metabolism, result in distubances of cerebral circulation and further aggravate cerebral edema. Therefore, increased intracranial pressure exerts serious damaging effects on patients or is sometimes fatal to them.

As a result of various investigations, we have now found that the piperazine derivative (I) of the present invention shows a significant decrease in intracranial pressure. For example, when a solution of a test compound in an aqueous 5 w/v % mannitol solution was infused via the femoral vein of rats at a rate of 0.2 ml/kg/minute for 20 minutes, 1-[3-(4-acetamido-2-methoxyphenoxy)-n-propyl]-4-(3-fluorophenyl)-piperazine dose: 1 mg/kg) showed about 27% decrease in the intracranial pressure 40 minutes after administration of the test compound.

In view of the effect of the piperazine derivative (I) on intracranial pressure, said compound of the present invention is useful for treating a warm-blooded animal, including human, suffering from increased intracranial pressure due to various cerebral diseases such as cerebral infarction, cerebral thrombosis, cerebral embolism, cerebral hemorrhage, subarachnoid hemorrhage, head injury, cerebral tumor, cerebral edema, encephalomyelitis and the like.

Moreover, since the piperazine derivative (I) of the present invention has a potent depressing effect on central nervous system, said compound is also useful as tranquilizers, analgesics and/or anti-vomitting agents.

The compound (I) of the present invention can be used for pharmaceutical use either as the free base or as a pharmaceutically acceptable acid addition salt thereof. Pharmaceutically acceptable acid addition salts of the compound (I) include, for example, inorganic acid addition salts (e.g., hydrochloride, hydrobromide, sulfate, nitrate, phosphate) and organic acid addition salts (e.g., acetate, lactate, oxalate, citrate, tartrate, fumarate, maleate, methanesulfonate, benzoate). The compound (I) of the present invention can be administered either orally or parenterally. A daily dose of the compound (I) may be about 0.05 to 50 mg (in terms of free base), especially 0.1 to 10 mg (in terms of free base), per kilogram of body weight. Further, the compound (I) may be used in the form of a pharmaceutical preparation containing the same compound in conjunction or admixture with a pharmaceutical excipient suitable for enteral or parenteral administration. Suitable excipients include, for example, gelatin, lactose, glucose, sodium chloride, starch, magnesium stearate, talcum, vegetable oil and other known excipients. The pharmaceutical preparations may be in solid form such as powder, tablets or capsules; or in liquid form such as solutions, suspensjions or emulsions. The compound (I) may also be used in the form of an injection for drip infusion.

Examples of the piperazine derivative of the invention include those of the formula (I) in which $R^1$ is hydrogen, alkyl ($C_{1-8}$) (e.g., methyl, ethyl, propyl, butyl), alkyl ($C_{1-4}$)-sulfonyl (e.g., methylsulfonyl, ethylsulfonyl) or an acyl group of the formula: $R^3CO-$ (wherein $R^3$ is hydrogen, alkyl ($C_{1-7}$) (e.g., methy, ethyl, propyl, isopropyl, butyl, t-butyl, pentyl), halogenoalkyl ($C_{1-4}$) (e.g., trifluoromethyl), alkoxy ($C_{1-4}$)-carbonyl-alkyl ($C_{1-4}$) (e.g., 2-methoxycarbonylethyl, 2-ethoxycarbonylethyl, cycloalkyl ($C_{3-6}$) (e.g., cyclopropyl, cyclopentyl, cyclohexyl), alkenyl ($C_{2-5}$) (e.g., 2-methyl-1-propenyl) alkoxy ($C_{1-4}$) (e.g., methoxy, ethoxy, propoxy, isopropoxy, butoxy, t-butoxy), amino, alkyl ($C_{1-4}$)-amino (e.g., methylamino, ethylamino) or anilino; $R^2$ is hydrogen, alkyl ($C_{1-4}$) (e.g., methyl, ethyl, propyl, butyl), alkoxy ($C_{1-4}$)-carbonyl-alkyl ($C_{1-4}$) (e.g., 1-methoxycarbonylethyl, 1-ethoxycarbonylethyl), carboxy-alkyl ($C_{1-4}$) (e.g., 1-carboxyethyl), alkenyl ($C_{2-5}$) (e.g., 3-methyl-2-butenyl) or alkyl ($C_{1-4}$)-sulfonyl (e.g., methylsulfonyl, ethylsulfonyl); or $R^1$ and $R^2$ are combined together to form succinyl group; Ring A is phenyl, alkyl ($C_{1-4}$)-phenyl (e.g., 2-methylphenyl, 3-methylphenyl, 4-methylphenyl) or halogenophenyl (e.g., 2-chlorophenyl, 3-chlorophenyl, 4-chlorophenyl, 2-fluorophenyl, 3-fluorophenyl, 4-fluorophenyl); and n is an integer of 2 to 6. Among the piperazine derivatives of the present invention, a preferred subgenus includes the compound of the formula (I) in which $R^1$ is hydrogen, alkyl ($C_{1-8}$), alkyl ($C_{1-4}$)-sulfonyl, formyl, alkyl ($C_{1-7}$)-carbonyl, cycloalkyl ($C_{3-6}$)-carbonyl, alkenyl ($C_{2-5}$)-carbonyl, alkoxy ($C_{1-4}$)-carbonyl or carbamoyl; $R^2$ is hydrogen, alkyl ($C_{1-4}$) or carboxy-alkyl ($C_{1-4}$); Ring A is phenyl, alkyl ($C_{1-4}$)-phenyl or halogenophenyl; and n is 2 to 4. Another preferred subgenus includes the compound of the formula (I) in which $R^1$ is hydrogen, alkyl ($C_{1-8}$), formyl, alkyl ($C_{1-7}$)-carbonyl, cycloalkyl ($C_{3-6}$)-carbonyl, alkenyl ($C_{2-5}$)-carbonyl or alkoxy ($C_{1-4}$)-carbonyl; $R^2$ is hydrogen, alkyl ($C_{1-4}$) or carboxy-alkyl ($C_{1-4}$); Ring A is phenyl, methylphenyl, chlorophenyl or fluorophenyl; and n is 3 to 4. Other preferred subgenus includes the compound of the formula (I) in which $R^1$ is hydrogen, methyl, ethyl, formyl, acetyl, isopropylcarbonyl, t-butylcarbonyl, cyclopropylcarbonyl, cyclohexylcarbonyl, 2-methyl-1-propenyl-carbonyl, ethoxycarbonyl or t-butoxycarbonyl; $R^2$ is hydrogen, methyl or 1-carboxyethyl; Ring A is phenyl, 3-methylphenyl, 2-fluorophenyl or 3-fluorophenyl; and n is 3 or 4. Further preferred subgenus includes the compound of the formula (I) in which $R^1$ is hydrogen, methyl, ethyl, acetyl or t-butoxycarbonyl; $R^2$ is hydrogen or methyl; Ring A is phenyl, 3-methylphenyl, 2-fluorophenyl or 3-fluorophenyl; and n is 3.

According to the present invention, the compound (I) can be prepared by any one of the methods (A) through (J) described in the following schemes.

Method (A)

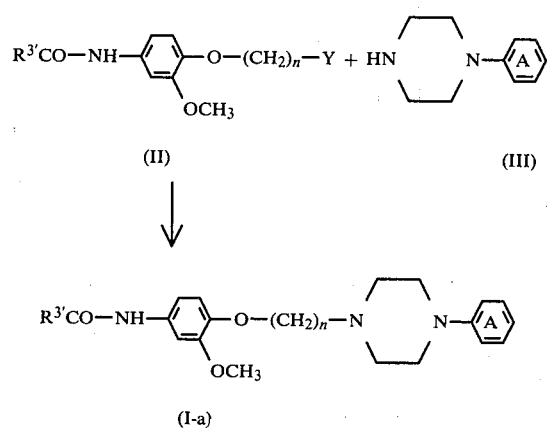

(In the above-mentioned reaction scheme, $R^{3'}$ is alkyl ($C_{1-7}$), Y is a reactive group or atom, and Ring A and n are the same as defined above.)

Method (B)

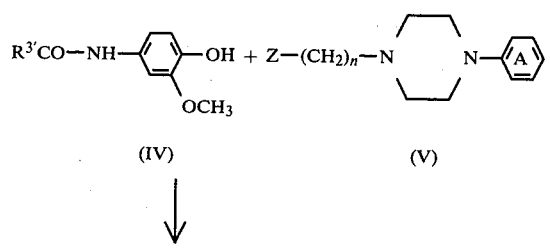

(In the above-mentioned reaction scheme, Z is a reactive group or atom, and $R^{3'}$, Ring A and n are the same as defined above.).

Method (C)

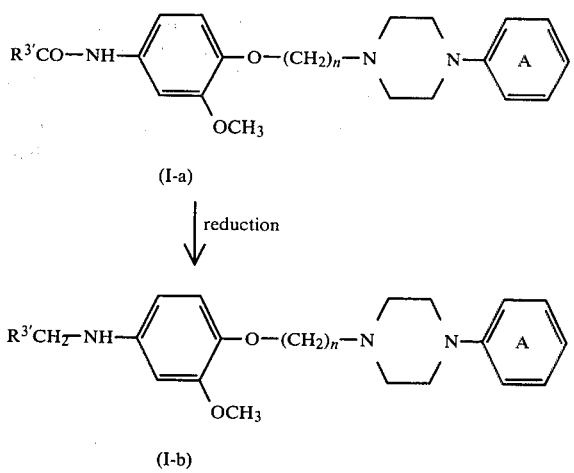

(In the above-mentioned reaction scheme, $R^{3'}$, Ring A and n are the same as defined above.)

Method (D)

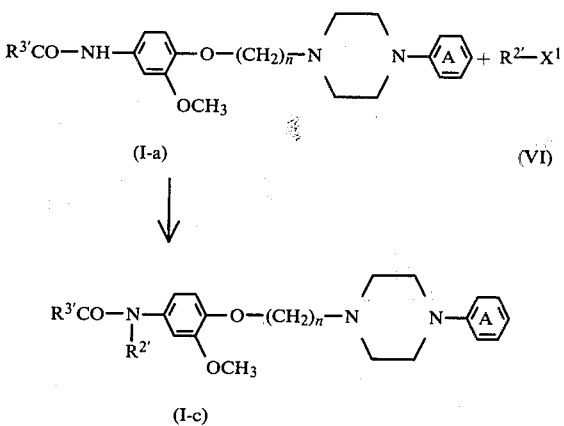

(In the above-mentioned reaction scheme, $R^{2'}$ is alkenyl ($C_{2-5}$) or alkoxy ($C_{1-4}$)-carbonyl-alkyl ($C_{1-4}$), $X^1$ is halogen, and $R^{3'}$, Ring A and n are the same as defined above.)

Method (E)

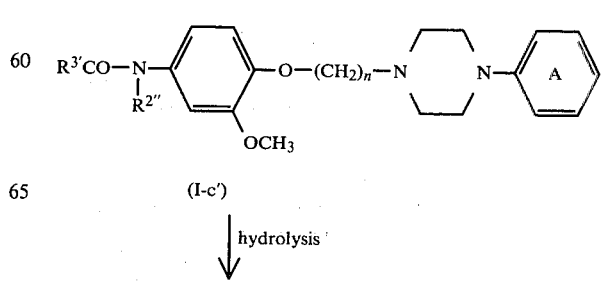

hydrolysis

-continued

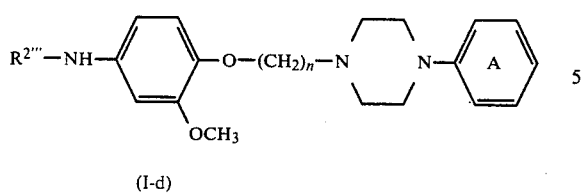

(I-d)

(In the above-mentioned reaction scheme, $R^{2''}$ is hydrogen, alkenyl ($C_{2-5}$) or alkoxy ($C_{1-4}$)-carbonyl-alkyl ($C_{1-4}$), $R^{2'''}$ is hydrogen, alkenyl ($C_{2-5}$) or carboxy-alkyl ($C_{1-4}$), and $R^{3'}$, Ring A and n are the same as defined above.)

Method (F)

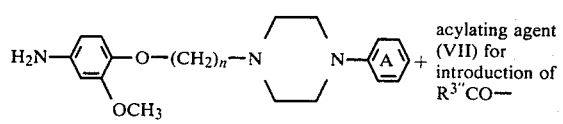

(I-d')

↓

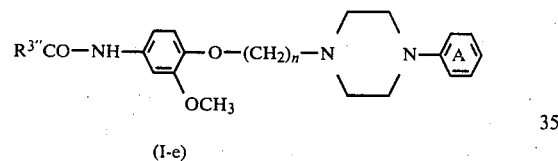

(I-e)

(In the above-mentioned reaction scheme, $R^{3''}$ is hydrogen, alkyl ($C_{1-7}$), cycloalkyl ($C_{3-6}$), alkenyl ($C_{2-5}$), alkoxy ($C_{1-4}$), alkoxy ($C_{1-4}$)-carbonyl-alkyl ($C_{1-4}$) or halogenoalkyl ($C_{1-4}$), and Ring A and n are the same as defined above.)

Method (G)

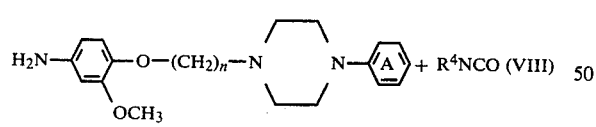

(I-d')

↓

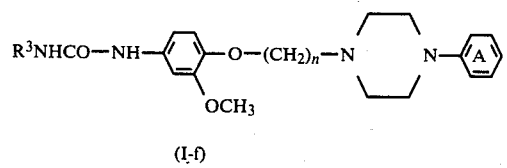

(I-f)

(In the above-mentioned reaction scheme, $R^4$ is hydrogen, alkyl ($C_{1-4}$) or phenyl, and Ring A and n are the same as defined above.)

Method (H)

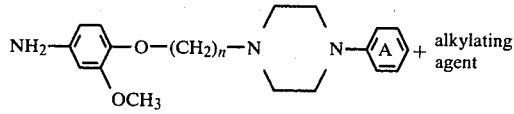

(I-d')

↓

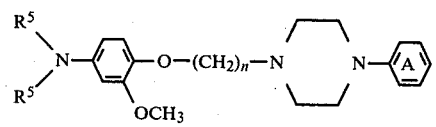

(I-g)

(In the above-mentioned reaction scheme, $R^5$ is alkyl ($C_{1-4}$), and Ring A and n are the same as defined above.)

Method (I)

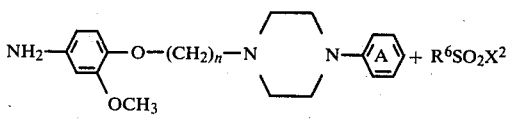

(I-d')                                        (IX)

↓

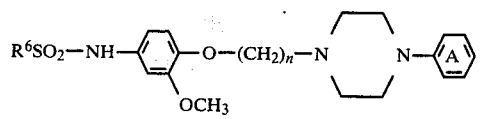

(I-h)

and

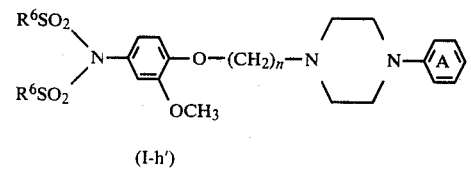

(I-h')

(In the above-mentioned reaction scheme, $R^6$ is alkyl ($C_{1-4}$), $X^2$ is halogen, and Ring A and n are the same as defined above.)

Method (J)

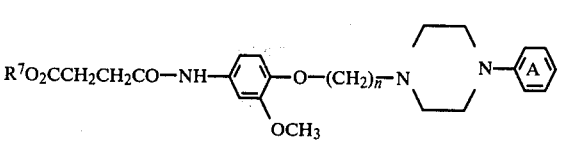

(I-e')

↓ heating

↓

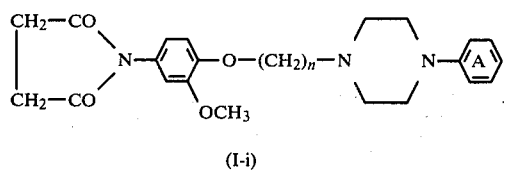

(I-i)

(In the above-mentioned reaction scheme, $R^7$ is alkyl ($C_{1-4}$), and Ring A and n are the same as defined above.)

Method (A)

The method (A) comprises condensing the compound (II) with the compound (III) to give the compound (I-a) (i.e., the compound of the formula (I) in which $R^1$ is alkyl ($C_{1-7}$)-carbonyl and $R^2$ is hydrogen). Examples of the reactive group or atom (Y) in the starting compound (II) include alkylsulfonyloxy (e.g., methylsulfonyloxy), arylsulfonyloxy (e.g., p-toluenesulfonyloxy) and halogen atom (e.g., chlorine, bromine). The reaction may be accomplished in a solvent in the presence of an acid acceptor. Alkanol (e.g., methanol, ethanol, isopropanol), dimethylformamide, dimethylsulfoxide and the like are suitable as the solvent. Examples of the acid acceptor include organic bases such as triethylamine, triethylenediamene or N-methylpiperidine; and inorganic bases such as potassium carbonate, sodium carbonate, potassium bicarbonate or sodium bicarbonate. When an excess of the compound (III) is used in the reaction, it is not always necessary to use the above-mentioned acid acceptor because said compound (III) serves as the acid acceptor. It is preferred to carry out the reaction at a temperature of 20° to 100° C.

Method (B)

the method (B) comprises condensing the compound (IV) with the compound (V) to give the compound (I-a). Examples of the reactive group of atom (Z) in the compound (V) include alkylsulfonyloxy (e.g., methylsulfonyloxy), arylsulfonyloxy (e.g., p-toluenesulfonyloxy) and halogen atom (e.g., chlorine, bromine). The reaction may be accomplished in a solvent in the presence of an acid acceptor. Alkanol (e.g., methanol, ethanol, isopropanol), dimethylformamide, dimethylsulfoxide and the like are suitable as the solvent. Examples of the acid acceptor include inorganic bases such as sodium hydroxide, potassium hydroxide, lithium hydroxide and the like. It is preferred to carry out the reaction at a temperature of 20° to 100° C. It is also preferred to carry it out in an inert gas (e.g., nitrogen gas) atmosphere.

Method (C)

The method (C) comprises reducing the compound (I-a) to give the compound (I-b) (i.e., the compound of the formula (I) in which $R^1$ is alkyl ($C_{2-8}$) and $R^2$ is hydrogen). The reduction reaction may be accomplished by treating the compound (I-a) with a reducing agent in a solvent. Examples of the reducing agent include lithium aluminum hydride, aluminum trihydride, trialkoxylithium aluminum hydride (e.g., trimethoxylithium aluminum hydride), diborane and the like. Ether, tetrahydrofuran, dioxane, 1,2-dimethoxyethane and the like are suitable as the solvent. It is preferred to carry out the reaction at a temperature of $-10°$ to 30° C.

Method (D)

The method (D) comprises reacting the compound (I-a) with the compound (VI) to give the compound (I-c) (i.e., the compound of the formula (I) in which $R^1$ is alkyl ($C_{1-7}$)-carbonyl and $R_2$ is alkenyl ($C_{2-5}$) or alkoxy ($C_{1-4}$)-carbonyl-alkyl ($C_{1-4}$)). The reaction of the compound (I-a) with the compound (VI) may be accomplished in a solvent in the presence of an acid acceptor. Benzene, toluene, dimethylformamide, dioxane, dimethylsulfoxide and the like are suitable as the solvent. Examples of the acid acceptor include sodium hydride, sodium amide, sodium alkoxide (e.g., sodium methoxide, sodium ethoxide) and the like. It is preferred to carry out the reaction at a temperature of 20° to 100° C.

Method (E)

The method (E) comprises hydrolyzing the compound (I-c') to give the compound (I-d) (i.e., the compound of the formula (I) in which $R^1$ is hydrogen and $R^2$ is hydrogen, alkenyl ($C_{2-5}$) of carboxy-alkyl ($C_{1-4}$)). The hydrolysis of the compound (I-c') may be accomplished by treating said compound with an acid in a solvent. Examples of the acid include mineral acids such as hydrochloric acid, sulfuric acid and the like. Water and aqueous alkanol (e.g., aqueous methanol, aqueous ethanol) are suitable as the solvent. It is preferred to carry out the reaction at a temperature of 20° to 150° C. When a compound of the formula (I-c') in which $R^{2''}$ is alkoxy ($C_{1-4}$)-carbonyl-alkyl ($C_{1-4}$) is employed as the starting compound in the above-mentioned reaction, said compound is deacylated and at the same time hydrolyzed at the ester position thereof to give a compound of the formula (I-d) in which $R^{2''}$ is carboxy-alkyl ($C_{1-4}$).

Method (F)

The method (F) comprises reacting the compound (I-d') with the acylating agent (VII) to give the compound (I-e) (i.e., the compound of the formula (I) in which $R^1$ is an acyl group shown by the formula: $R^{3''}$CO— (wherein $R^{3''}$ is hydrogen, alkyl ($C_{1-7}$), cycloalkyl ($C_{3-6}$), alkenyl ($C_{2-5}$), alkoxy ($C_{1-4}$), alkoxy ($C_{1-4}$)-carbonyl-alkyl ($C_{1-4}$) or halogenoalkyl ($C_{1-4}$)) and $R^2$ is hydrogen). In the case where formyl group is introduced into the compound (I-d'), an alkyl formate is preferably employed as the acylating agent. On the other hand, an alkoxycarbonyl halide or 2-(alkoxycarbonylthio)-4,6-dimethylpyridine is employed as the acylating agent for introducing an alkoxycarbonyl group. Further, the introduction of a substituted or unsubstituted alkanoyl or alkenylcarbonyl group is accomplished by using the corresponding acid halide or acid anhydride as the acylating agent. The acylation reaction may be carried out in a solvent in the presence of absence of an acid acceptor. Methylene chloride, tetrahydrofuran, benzene, chloroform and the like are suitable as the solvent. Examples of the acid acceptor include organic bases such as triethylamine, pyridine and the like; and inorganic bases such as sodium carbonate, potassium carbonate and the like. It is preferred to carry out the reaction at a temperature of $-10°$ to 70° C. In carrying out the reaction by using ethyl formate as the acylating agent or by using pyridine as the acid acceptor, it is not always necessary to use the solvent because ethyl formate and pyridine serve as the solvent.

Method (G)

The method (G) comprises reacting the compound (I-d') with the compound (VIII) to give the compound (I-f) (i.e., the compound of the formula (I) in which R¹ is carbamoyl, alkyl (C₁₋₄)-carbamoyl or phenyl-carbamoyl and R² is hydrogen). The reaction of the compound (I-d') with the compund (VIII) may be carried out in a solvent. When isocyanic acid (HNCO) is employed as the compound (VIII), it is preferred to prepare said compound by reacting an alkali metal isocyanate (e.g., potassium isocyanate) with an acid (e.g., hydrochloric acid) in a solution containing the compound (I-d'). Examples of the solvent include tetrahydrofuran, benzene, dioxane, toluene, xylene and the like. It is preferred to carry out the reaction at a temperature of 10° to 100° C.

Method (H)

The method (H) comprises reacting the compound (I-d') with an alkylating agent to give the compound (I-g) (i.e., the compound of the formula (I) in which R¹ and R² are alkyl (C₁₋₄)). Trialkyl phosphate (e.g., trimethyl phosphate, triethyl phosphate, tributyl phosphate) is suitable as the alkylating agent. When said trialkyl phosphate is employed as the alkylating agent, it is preferred to carry out the reaction by heating a mixture of the compound (I-d') and the trialkyl phosphate at a temperature of 150° to 230° C.

Method (I)

The method (I) comprises reacting the compound (I-d') with the compound (IX) to give the compound (I-h) (i.e., the compound of the formula (I) in which R¹ is alkyl (C₁₋₄)-sulfonyl and R² is hydrogen) and the compound (I-h') (i.e., the compound of the formula (I) in which R¹ and R² are alkyl (C₁₋₄)-sulfonyl). The reaction of the compound (I-d') with the compound (IX) may be carried out in a solvent in the presence of an acid acceptor. Methylene chloride, tetrahydrofuran, benzene, chloroform and the like are suitable as the solvent. Examples of the acid acceptor include organic bases (e.g., triethylamine, pyridine) and inorganic bases (e.g., potassium carbonate, sodium carbonate). It is preferred to carry out the reaction at a temperature of −10° to 50° C. The compounds (I-h) and (I-h') which are prepared in the above-mentioned reaction may be readily separated from each other by a conventional method, for example, by silica gel chromatography.

Method (J)

The method (J) comprises heating the compound (I-e') to give the compound (I-i) (i.e., the compound of the formula (I) in which R¹ and R² are combined together to form succinyl group). The reaction may be carried out by heating the compound (I-e') at 100° to 200° C. in a solvent. Xylene, toluene, mesitylene and the like are suitable as the solvent.

The starting compounds of the present invention, i.e., the compounds (II) and (V), may be prepared by the methods described in the following reaction schemes.

Synthesis of the compound (II)

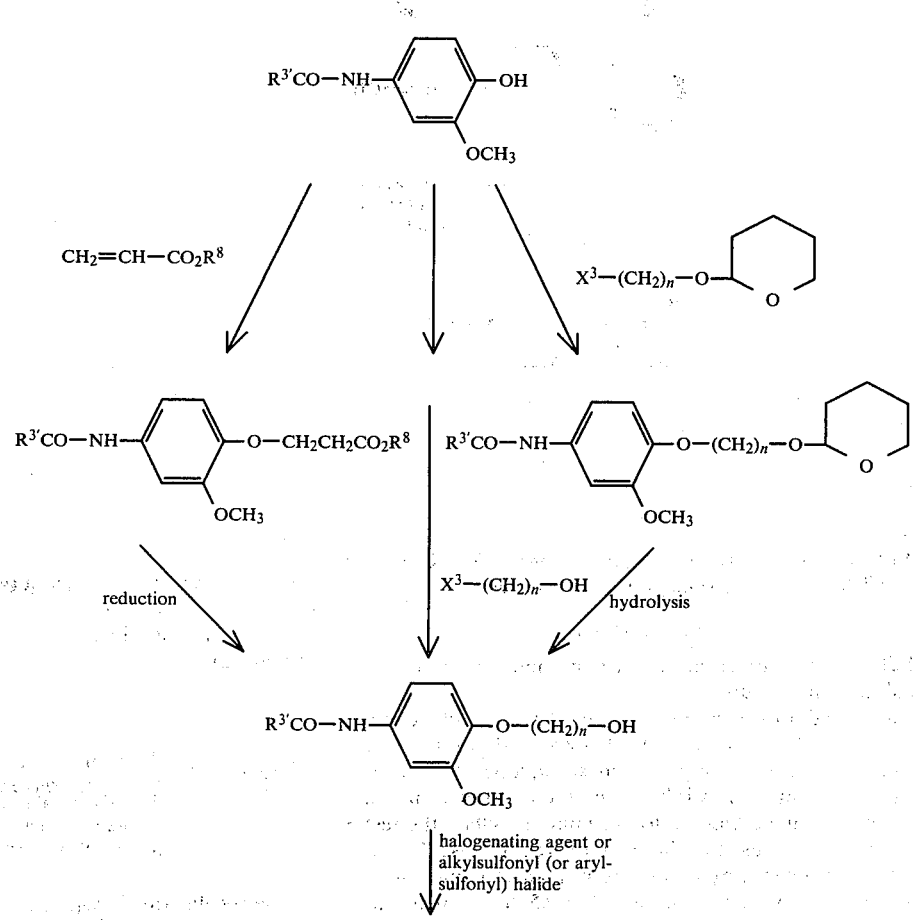

-continued

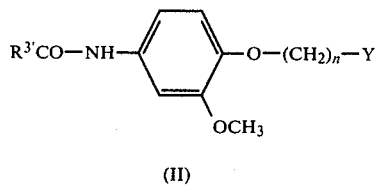

(II)

(In the above-mentioned reaction scheme, $R^8$ is alkyl ($C_{1-4}$), $X^3$ is halogen, and $R^{3'}$, Y and n are the same as defined above.)

Synthesis of the compound (V)

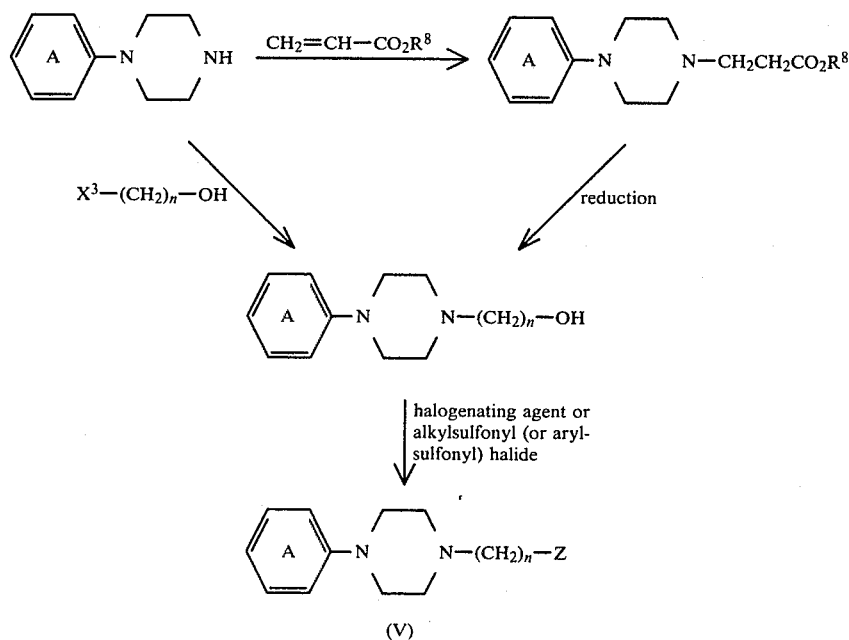

(V)

(In the above-mentioned reaction scheme, $R^8$, Ring A, Z, $X^3$ and n are the same as defined above.)

Experiment 1

(Effect of i.v. injection of test compounds on intracranial pressure in rats)

Male SD-rats weighing 500 to 800 g (each group consisting of 5 rats) were anesthetized with urethane. A solution of a test compound in an aqueous 5 w/v % mannitol solution was infused via the femoral vein at a rate of 0.2 ml/kg/minute for 20 minutes (when the test compound was used in the form of free base, said solution was prepared by dissolving it in an aqueous 5 w/v % mannitol solution with the aid of 0.5 N hydrochloric acid). Intracranial pressure (i.e., cerebrospinal fluid pressure in the cisterna magna) was continuously monitored via a cannula inserted in the cisterna magna. The cannula was connected to a transducer, and recording were made on graph paper. The effect of the test compound on the intracranial pressure was estimated in terms of the increase or decrease in intracranial pressure, which was calculated in accordance with the following formula:

$$\text{Changes (\%) in intracranial pressure} = \left[ \frac{\text{Intracranial pressure (mm H}_2\text{O) measured after administration of test compound}}{\text{Intracranial pressure (mm H}_2\text{O) measured before administration of test compound}} \right] \times 100$$

The results are shown in the following Table 1.

TABLE 1

Structure: R¹R²N—[phenyl with OCH₃]—O—(CH₂)ₙ—N(piperazine)N—Ring A (Dose: one mg/kg, i.v.)

| NO. | R¹ | R² | n | Ring A | Salt | 0* | 40 | 60 | 120 | 180 |
|---|---|---|---|---|---|---|---|---|---|---|
| 1 | $CH_3CO-$ | H | 3 | phenyl-CH₃ | — | 100 | 82.6 | 83.1 | 83.5 | 83.6 |
| 2 | " | " | " | phenyl-F | — | 100 | 73.1 | 74.4 | 76.6 | 83.6 |
| 3 | " | " | 4 | phenyl-F | $CH_3SO_3H$ | 100 | 86.6 | 91.9 | 85.7 | 84.6 |
| 4 | $CH_3CH_2-$ | " | 3 | phenyl | HCl | 100 | 83.9 | 81.1 | 86.8 | 91.3 |
| 5 | H | " | " | " | " | 100 | 79.1 | 77.0 | 75.0 | 75.6 |
| 6 | " | $CH_3-CH(COOH)-$ | " | " | " | 100 | 81.5 | 86.2 | 96.2 | 99.0 |
| 7 | $HCO-$ | H | " | " | — | 100 | 84.1 | 83.5 | 83.5 | 81.9 |
| 8 | $(CH_3)_2CHCO-$ | " | " | " | — | 100 | 83.3 | 85.4 | 85.1 | 87.1 |
| 9 | $(CH_3)CCO-$ | " | " | " | — | 100 | 84.1 | 84.9 | 84.9 | 87.4 |
| 10 | cyclopropyl-CO— | " | " | " | — | 100 | 85.9 | 84.3 | 83.6 | 86.2 |
| 11 | cyclohexyl-CO— | " | " | " | — | 100 | 91.1 | 94.3 | 78.7 | 78.8 |
| 12 | $(CH_3)_2C=CHCO-$ | " | " | " | — | 100 | 76.7 | 84.3 | 91.9 | 93.5 |
| 13 | $CH_3CH_2OCO-$ | " | " | " | $CH_3SO_3H$ | 100 | 79.7 | 79.3 | 79.2 | 82.2 |
| 14 | $(CH_3)_3COCO-$ | " | " | " | — | 100 | 78.9 | 77.7 | 80.3 | 81.6 |
| Control | 5 w/v % mannitol solution (4 ml/kg, i.v.) | | | | | 100 | 106.4 | 107.5 | 114.4 | 110.7 |

Column headers: Change in intracranial pressure (%), Time after administration of test compound (minute): 0*, 40, 60, 120, 180

Note:
*The intracranial pressure measured before administ-administration of test compound was 71.5 ± 3.5 mm H₂O.

Experiment 2

(Inhibitory effect of test compound on central nervous system in mice)

Inhibitory effect of test compound on central nervous system was examined by the following methods.

(1) Inhibitory effect on spontaneous motor activity

A solution or suspension of a test compound in water or an aqueous carboxymethylcellulose solution was administered intraperitoneally to male mice weighing 18 to 20 g (each group consisting of 5 mice). Thirty minutes after administration of the test compound, the spontaneous motor activity of the mice was measured with an animex activity meter for 5 minutes. The 50% effective dose ($ED_{50}$) of the test compound was estimated in terms of dose which is necessary to decrease the motor activity of the medicated mice by 50% of that of a control group (i.e., non-medicated mice). The results are shown in Table 2.

(2) Effect on sodium hexobarbital-induced anesthesia

A solution or suspension of a test compound in water or an aqueous carboxymethylcellulose solution was administered intraperitoneally to male mice weighing 18 to 20 g (each group consisting of 5 mice). Thirty minutes after intraperitoneal administration of the test compound, sodium hexobarbital (100 mg/kg) was administered intraperitoneally to the mice, and the sleeping time between the loss and recovery of righting reflex was measured. The 50% effective dose ($ED_{50}$) of the test compound was estimated in terms of dose which is necessary to prolong the sleeping time of the medicated mice twice as long as that of a control group (i.e., non-medicated mice). The results are shown in Table 3.

(3) Anti-apomorphine activity

A solution or suspension of a test compound in water or an aqueous carboxymethylcellulose solution was administered intraperitoneally to male mice weighing 18 to 20 g (each group consisting of 5 mice). Thirty minutes after administration of the test compound, apomorphine hydrochloride (2.5 mg/kg) was administered subcutaneously to the mice, and the number of the mice which could climb a cage was examined. The 50% effective dose ($ED_{50}$) of the test compound was estimated in terms of dose which is necessary to decrease the number of the medicated mice which could climb the cage by 50% of the number of a control group (i.e., non-medicated mice) which could climb the cage. The results are shown in Table 4.

TABLE 2

| NO. | $R^1$ | $R^2$ | n | Ring A | Salt | Inhibitory effect on spontaneous motor activity ($ED_{50}$, mg/kg) |
|---|---|---|---|---|---|---|
| 1 | $CH_3CO-$ | H | 3 |  F | — | 0.9 |
| 2 | " | " | " |  $CH_3$ | — | 0.9 |
| 3 | " | " | " |  Cl | — | 0.9 |
| 4 | " | " | " |  F | $CH_3SO_3H$ | 0.5 |
| 5 | H | " | " | 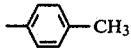 | — | 0.7 |

TABLE 3

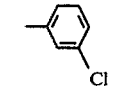

| NO. | $R^1$ | $R^2$ | n | Ring A | Salt | Effect on sodium hexobarbital-induced anesthesia ($ED_{50}$, mg/kg) |
|---|---|---|---|---|---|---|
| 1 | $CH_3CO-$ | H | 3 | 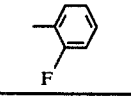—$CH_3$ | — | 2.1 |
| 2 | " | " | " | —⟨⟩—Cl | — | 2.8 |
| 3 | " | " | " | —⟨⟩—F | $CH_3SO_3H$ | 1.3 |

TABLE 4

| NO. | $R^1$ | $R^2$ | n | Ring A | Salt | Anti-apomorphine activity ($ED_{50}$, mg/kg) |
|---|---|---|---|---|---|---|
| 1 | H | H | 3 | —⟨⟩ | — | 1.6 |

TABLE 4-continued

| NO. | R¹ | R² | n | Ring A | Salt | Anti-apomorphine activity ($ED_{50}$, mg/kg) |
|---|---|---|---|---|---|---|
| 2 | $CH_3CO-$ | " | " |  (2-F phenyl) | $CH_3SO_3H$ | 2.8 |
| 3 | $C_2H_5OCO-$ | " | " | phenyl | $CH_3SO_3H$ | 3.0 |

Experiment 3

A solution or suspension of a test compound in water or an aqueous carboxymethylcellulose solution was administered intraperitoneally to male mice weighing 18 to 22 g (each group consisting of 5 mice), and the mice were observed for 72 hours after administration of the test compound. As a result, the maximum tolerance doses of 1-[3-(4-acetamido-2-methoxyphenoxy)-n-propyl]-4-(3-fluorophenyl)-piperazine, 1-[3-(4-acetamido-2-methoxyphenoxy)-n-propyl]-4-(2-fluorophenyl)-piperazine and 1-[3-(4-ethoxycarbonylamino-2-methoxyphenoxy)-n-propyl]-4-phenyl-piperazine methanesulfonate were more than 300 mg/kg.

EXAMPLE 1

620 mg of 4-(4-methylphenyl)piperazine and 355 mg of triethylamine are added to a solution of 1.3 g of 1-(4-acetamido-2-methoxyphenoxy)-3-(p-toluenesulfonyloxy)-n-propane in 40 ml of ethanol, and the mixture is refluxed for 6 hours. After the reaction, the mixture is evaporated under reduced pressure to remove ethanol. The residue is adjusted to pH 11 with a cold aqueous saturated sodium hydroxide solution, and then extracted with chloroform. The extract is washed with water and an aqueous saturated sodium chloride solution, successively. Said extract is dried and then evaporated under reduced pressure. The residue is recrystallized from acetone, whereby 890 mg of 1-[3-(4-acetamido-2-methoxyphenoxy)-n-propyl]-4-(4-methylphenyl)-piperazine are obtained as colorless leaflets. The mother liquor is concentrated under reduced pressure, and the residue is purified by silica gel chromatography (Solvent; 3% methanol/chloroform). 270 mg of the same product as obtained above are obtained. Total yield: 88.5%

M.p. 144° C.–145° C.

IR $\nu_{max}^{Nujol}$ (cm$^{-1}$): 3250, 1650, 1140, 1040

NMR (CDCl$_3$)δ: 7.92 (broad s, $-N\underline{H}-$), 7.32 (d, 1H, J=1.5 Hz, aromatic), 7.3–6.8 (m, 2H, aromatic), 7.10 (d, 2H, J=8.9 Hz, aromatic), 68.4 (d, 2H, J=8.9 Hz, aromatic), 4.06 (t, 2H, J=6.0 Hz, $-OC\underline{H}_2CH_2-$), 3.80 (s, 3H, $-OCH_3$), 3.16 (m, 4H), 2.58 (m, 6H), 2.26 (s, 3H, $-Ph-C\underline{H}_3$), 2.11 (s, 3H, $C\underline{H}_3CONH-$), 2.00 (m, 2H)

Mass m/e: 397 (M$^+$), 189 (base peak)

EXAMPLE 2

1.3 g of 1-(4-acetamido-2-methoxyphenoxy)-3-(p-toluenesulfonyloxy)-n-propane, 690 mg of 4-(4-chlorophenyl)piperazine, 355 mg of triethylamine and 40 ml of ethanol are treated in the same manner as described in Example 1. The crude product thus obtained is recrystallized from acetone, whereby 1.22 g of 1-[3-(4-acetamido-2-methoxyphenoxy)-n-propyl]-4-(4-chlorophenyl)-piperazine are obtained as colorless needles. Yield: 85.5%

M.p. 152° C.–153° C.

IR $\nu_{max}^{Nujol}$ (cm$^{-1}$): 3320, 1650, 1055, 1045

NMR (CDCl$_3$)δ: 7.75 (broad s, 1H, $-N\underline{H}-$), 7.30 (broad s, 1H, aromatic), 7.22 (d, 2H, J=9 Hz, aromatic), 7.1–6.8 (m, 2H, aromatic), 6.82 (d, 2H, J=9 Hz, aromatic), 4.07 (t, 2H, J=5.9 Hz, $-OC\underline{H}_2CH_2-$), 3.82 (s, 3H, $-OC\underline{H}_3$), 3.4–3.0 (m, 4H), 2.8–2.4 (m, 6H), 2.3–1.8 (m, 2H), 2.12 (s, 3H, $C\underline{H}_3CONH-$)

Mass m/e: 419, 417 (M$^+$), 211 209 (base peak)

EXAMPLE 3

1.3 g of 1-(4-acetamido-2-methoxyphenoxy)-3-(p-toluenesulfonyloxy)-n-propane, 630 mg of 4-(4-fluorophenyl)piperazine, 355 mg of triethylamine and 40 ml of ethanol are treated in the same manner as described in Example 1. The crude product thus obtained is recrystallized from acetone, whereby 1.18 g of 1-[3-(4-acetamido-2-methoxyphenoxy)-n-propyl]-4-(4-fluorophenyl)-piperazine are obtained as colorless prisms. Yield: 89%

M.p. 137° C.–138° C.

IR $\nu_{max}^{Nujol}$ (cm$^{-1}$): 3250- 3070, 1650, 1135, 1040

NMR (CDCl$_3$)δ: 7.92 (broad s, 1H, N$\underline{H}$), 7.36 (d, 1H, J=1.5 Hz, aromatic), 7.2–6.7 (m, 6H, aromatic), 4.09 (t, 2H, J=6.6 Hz, $-OC\underline{H}_2CH_2-$), 3.84 (s, 3H, $-OC\underline{H}_3$), 3.4–2.9 (m, 4H), 2.9–2.4 (m, 6H), 2.13 (s, 3H, $C\underline{H}_3CONH-$), 2.1–1.8 (m, 2H)

Mass m/e: 401 (M$^+$), 193 (base peak)

EXAMPLE 4

1.3 g of 1-(4-acetamido-2-methoxyphenoxy)-3-(p-toluenesulfonyloxy)-n-propane, 620 mg of 4-(3-methylphenyl)piperazine, 355 mg of triethylamine and 40 ml of ethanol are treated in the same manner as described in Example 1. The crude product thus obtained is recrystallized from acetone, whereby 1.21 g of 1-[3-(4-acetamido-2-methoxyphenoxy)-n-propyl]-4-(3-methylphenyl)-piperazine are obtained as colorless needles. Yield: 92.1%

M.p. 113° C.–114° C.

IR $\nu_{max}^{Nujol}$ (cm$^{-1}$): 3250, 1650, 1135, 1040

NMR (CDCl$_3$)δ: 7.79 (broad s, 1H, $-N\underline{H}-$), 7.6–6.5 (m, 7H, aromatic), 4.08 (t, 2H, J=6.5 Hz, $-OC\underline{H}_2C\underline{H}_2-$), 3.83 (s, 3H, $-OC\underline{H}_3$), 3.4–3.30 (m, 4H), 2.8–2.3 (m, 6H), 2.32 (s, 3H, $-Ph-C\underline{H}_3$), 2.3–1.8 (m, 2H), 2.12 (s, 3H, $C\underline{H}_3CONH-$)

Mass m/e : 397 (M+), 189 (base peak)

EXAMPLE 5

1.3 g of 1-(4-acetamido-2-methoxyphenoxy)-3-(p-toluenesulfonyloxy)-n-propane, 630 mg of 4-(3-fluorophenyl)piperazine, 355 mg of triethylamine and 40 ml of ethanol are treated in the same manner as described in Example 1. The crude product thus obtained is recrystallized from isopropyl alcohol, whereby 1.14 g of 1-[3-(4-acetamido-2-methoxyphenoxy)-n-propyl]-4-(3-fluorophenyl)-piperazine are obtained as colorless needles. Yield: 86%

M.p. 136° C.–137° C.

IR $\nu_{max}^{Nujol}$ (cm$^{-1}$) : 3275, 1660, 1135, 1035

NMR (CDCl$_3$)δ: 7.89 (broad s, 1H, —N$\underline{H}$—), 7.5–6.2 (m, 7H, aromatic), 4.10 (t, 2H, J=6.7 Hz, —OC$\underline{H}_2$C-H$_2$—), 3.84 (s, 3H, —OC$\underline{H}_3$), 3.4–3.0 (m, 4H), 2.8–2.3 (m, 6H), 2.3–1.8 (m, 2H), 2.13 (s, 3H, C$\underline{H}_3$CONH—)

Mass m/e : 401 (M+), 193 (base peak)

EXAMPLE 6

1.3 g of 1-(4-acetamido-2-methoxyphenoxy)-3-(p-toluenesulfonyloxy)-n-propane, 690 mg of 4-(2-chlorophenyl)piperazine, 355 mg of triethylamine and 40 ml of ethanol are treated in the same manner as described in Example 1. The crude product thus obtained is recrystallized from isopropyl alcohol, whereby 1.26 g of 1-[3-(4-acetamido-2-methoxyphenoxy)-n-propyl]-4-(2-chlorophenyl)-piperazine are obtained as colorless prisms. Yield: 91%

M.p. 115° C.–116° C.

IR $\nu_{max}^{Nujol}$ (cm$^{-1}$) : 3275, 1655, 1140, 1040

NMR (CDCl$_3$)δ: 7.84 (broad s, 1H, —N$\underline{H}$—), 7.6–6.8 (m, 7H, aromatic), 4.11 (t, 2H, J=6.5 Hz, —OC$\underline{H}_2$C-H$_2$—), 3.84 (s, 3H, —OC$\underline{H}_3$), 3.3–3.0 (m, 4H), 2.9–2.5 (m, 6H), 2.4–1.8 (m, 2H), 2.14 (s, 3H, C$\underline{H}_3$CONH—)

Mass m/e : 419, 417 (M+), 211, 209 (base peak)

EXAMPLE 7

1.3 g of 1-(4-acetamido-2-methoxyphenoxy)-3-(p-toluenesulfonyloxy)-n-propane, 630 mg of 4-(2-fluorophenyl)piperazine, 355 mg of triethylamine and 40 ml of ethanol are treated in the same manner as described in Example 1. The crude product thus obtained is recrystallized from isopropyl alcohol, whereby 1.23 g of 1-[3-(4-acetamido-2-methoxyphenoxy)-n-propyl]-4-(2-fluorophenyl)-piperazine are obtained as colorless needles. Yield: 92.5%

M.p. 122.5° C.–123.5° C.

IR $\nu_{max}^{Nujol}$ (cm$^{-1}$): 3270, 1655, 1140, 1040

NMR (CDCl$_3$)δ: 7.91 (broad s, 1H, —N$\underline{H}$—), 7.37 (broad s, 1H, aromatic), 7.2–6.7 (m, 6H, aromatic), 4.11 (t, 2H, J=6.6 Hz, —OC$\underline{H}_2$CH$_2$—), 3.84 (s, 3H, —OC$\underline{H}_3$), 3.3–2.9 (m, 4H), 2.8–2.3 (m, 6H), 2.3–1.8 (m, 2H), 2.14 (s, 3H, C$\underline{H}_3$CONH—)

Mass m/e : 401 (M+), 193 (base peak)

Hydrochloride:

M.p. 265° C.–268° C. (decomp.) (colorless needles, recrystallized from methanol)

IR $\nu_{max}^{Nujol}$ (cm$^{-1}$) : 3240–3100, 2600–2300, 1670, 1135, 1040

Methanesulfonate:

M.p. 196°–197° C. (colorless needles, recrystallized from ethanol)

IR $\nu_{max}^{Nujol}$ (cm$^{-1}$) : 3250–3100, 2700–2400, 1670, 1170, 1030, 1040

EXAMPLE 8

2.0 g of 1-(4-acetamido-2-methoxyphenoxy)-4-(p-toluenesulfonyloxy)-n-butane, 970 mg of 4-(2-fluorophenyl)piperazine, 550 mg of triethylamine and 30 ml of ethanol are treated in the same manner as described in Example 1. The crude product thus obtained is recrystallized from a mixture of isopropayl alcohol and isopropyl ether, whereby 1.3 g of 1-[4-(4-acetamido-2-methoxyphenoxy)-n-butyl]-4-(2-fluorophenyl)-piperazine are obtained as colorless needles. Yield: 64.7%

M.p. 115° C.–116.5° C.

IR $\nu_{max}^{Nujol}$ (cm$^{-1}$) : 3270, 3150, 1655, 1130, 1030,

NMR (CDCl$_3$)δ: 7.89 (broad s, 1H, —N$\underline{H}$—), 7.25–6.85 (m, 7H, aromatic), 3.98 (broad t, 2H, J=5.5 Hz, —OC$\underline{H}_2$CH$_2$—), 3.79 (s, 3H, —OC$\underline{H}_3$), 3.2–2.9 (m, 4H), 2.7–2.3 (m, 6H), 2.12 (s, 3H, C$\underline{H}_3$CONH—), 2.1–1.7 (m, 2H)

Mass m/e: 415 (M+), 235 (base peak), 193

Methanesulfonate:

M.p. 169° C.–170° C. (colorless plates, recrystallized from isopropyl alcohol)

IR $\nu_{max}^{Nujol}$ (cm$^{-1}$): 3250, 2700–2400, 1670, 1150, 1035

EXAMPLE 9

A mixture of 5 g of 1-(4-acetamido-2-methoxyphenoxy)-3-(p-toluenesulfonyloxy)-n-propane, 5.16 g of 4-phenylpiperazine and 100 ml of ethanol is refluxed for 4 hours. After the reaction, the mixture is evaporated under reduced pressure to remove the solvent. Water is added to the residue, and the aqueous mixture is extracted with methylene chloride. The extract is washed with water, dried and then evaporated under reduced pressure to remove the solvent. The residue is recrystallized from benzene, whereby 4.37 g of 1-[3-(4-acetamido-2-methoxyphenoxy)-n-propyl]-4-phenyl-piperazine are obtained as colorless needles. Yield: 90%

M.p. 136° C.–137° C.

IR $\nu_{max}^{Nujol}$ (cm$^{-1}$): 3240, 1650, 1130, 1040

NMR (CDCl$_3$)δ: 7.93 (broad s, 1H, —N$\underline{H}$—), 7.6–6.7 (m, 8H, aromatic), 4.08 (t, 2H, J=6.4 Hz, —OC$\underline{H}_2$C-H$_2$—), 3.82 (s, 3H, —OC$\underline{H}_3$), 3.5–3.1 (m, 4H), 2.8–2.4 (m, 6H), 2.35–1.8 (m, 2H), 2.12 (s, 3H, C$\underline{H}_3$CONH—)

Mass m/e: 383 (M+), 175 (base peak)

Hydrochloride:

M.p. 281° C.–283° C. (decomp.) (colorless needles, recrystallized from methanol)

IR $\nu_{max}^{Nujol}$ (cm$^{-1}$): 3230, 2450, 1655, 1600, 1130, 1035

Methanesulfonate:

M.p. 197° C.–199° C. (colorless needles, recrystallized from ethanol)

IR $\nu_{max}^{Nujol}$ (cm$^{-1}$): 3580, 3260, 1680, 1170, 1160, 1045

EXAMPLE 10

1.13 g of powdery sodium hydroxide are added under nitrogen atmosphere to a solution of 5.08 g of 4-acetamido-2-methoxyphenol in 70 ml of anhydrous dimethylsulfoxide. The mixture is stirred at 50° C. for 2 hours. A solution of 6 g of 1-(3-chloro-n-propyl)-4-(2-fluorophenyl)-piperazine in 20 ml of anhydrous dimethylsulfoxide is added dropwise at 20° C. to the mixture, and said mixture is stirred at 100° C. for 1.5 hours. After cooling, the reaction mixture is poured into ice-water. The crystalline precipitates are collected by filtration, whereby a crude product is obtained. The mother liquor obtained after isolating the crude product is extracted with chloroform. The extract is washed with water, dried and then evaporated under reduced pressure to remove the solvent, whereby another crude product is obtained. Both crude products obtained above are dissolved in hot isopropyl alcohol and then treated with activated charcoal. 6.95 of 1-[3-(4-acetamido-2-methoxyphenoxy)-n-propyl]-4-(2-fluorophenyl)-piperazine are thereby obtained as colorless needles. Yield: 74%

The physico-chemical properties of the product are identical with those of the sample obtained in Example 7.

EXAMPLE 11

200 mg of lithium aluminum hydride are suspended in 20 ml of anhydrous tetrahydrofuran under nitrogen atmosphere. A solution of 1.0 g of 1-[3-(4-acetamido-2-methoxyphenoxy)-n-propyl]-4-phenyl-piperazine in 20 ml of anhydrous tetrahydrofuran is added dropwise under ice-cooling to the suspension, and the mixture is stirred at 50° C. for 1.5 hours. Then, a mixture of tetrahydrofuran and water is added to the reaction mixture to decompose an excess of lithium aluminum hydride, and insoluble materials are removed by filtration. The filtrate is concentrated under reduced pressure to dryness. The residue is converted into its hydrochloride by using ethanolic hydrogen chloride, and then recrystallized from ethanol. 1.1 g of 1-[3-(4-ethylamino-2-methoxyphenoxy)-n-propyl]-4-phenyl-piperazine hydrochloride are thereby obtained as colorless needles. Yield: 86.6%

M.p. 237° C.–239° C.

IR $\nu_{max}^{Nujol}$ (cm$^{-1}$): 3380, 2700–2100, 1600, 1130, 1010

Mass m/e: 369 (M+), 203 (base peak), 175

EXAMPLE 12

A mixture of 23.6 g of 1-[3-(4-acetamido-2-methoxyphenoxy)-n-propyl]-4-phenyl-piperazine, 200 ml of 10% hydrochloric acid and 60 ml of conc. hydrochloric acid is refluxed for 2.5 hours. The mixture is adjusted to pH 11 by adding an aqueous 10% sodium hydroxide solution thereto. After cooling, the crystalline precipitates are collected by filtration, and then recrystallized from benzene. 14 g of 1-[3-(4-amino-2-methoxyphenoxy)-n-propyl]-4-phenyl-piperazine are thereby obtained.

The mother liquor obtained after isolating the product is concentrated under reduced pressure to dryness. The residue is purified by silica gel chromatography (Solvent; 1% methanol/chloroform), and then recrystallized from benzene, whereby 4.8 g of 1-[3-(4-amino-2-methoxyphenoxy)-n-propyl]-4-phenyl-piperazine are further obtained. Total yield: 89.5%

M.p. 112° C.–113° C.

IR $\nu_{max}^{Nujol}$ (cm$^{-1}$): 3560, 3430, 3350, 1600, 1030

NMR (CDCl$_3$)δ: 7.5–6.0 (m, 8H, aromatic), 4.00 (t, 2H, J=6.5 Hz, —OC$\underline{H}_2$CH$_2$—), 3.79 (s, 3H, —OC$\underline{H}_3$), 3.6–2.9 (m, 6H, disappeared by D$_2$O), 2.8–2.3 (m, 6H), 2.3–1.7 (m, 2H)

Mass m/e: 341 (M+), 203 (base peak), 175

EXAMPLE 13

250 mg of 65% sodium hydride are added under nitrogen atmosphere to a solution of 2.0 g of 1-[3-(4-acetamido-2-methoxyphenoxy)-n-propyl]-4-phenyl-piperazine in 40 ml of anhydrous dimethylformamide, and the mixture is stirred at room temperature overnight. A solution of 1.31 g of ethyl α-bromopropionate in 10 ml of anhydrous dimethylsulfoxide is added dropwise to the mixture, and said mixture is stirred at 50° C. to 55° C. for 24 hours. After the reaction, the mixture is poured into ice-water, and then extracted with ethyl acetate. The extract is washed with water, dried and then evaporated under reduced pressure to remove the solvent. The residue is purified by silica gel chromatography (Solvent; 2% methanol/chloroform), whereby 2.16 g of 1-{3-[4-(N-acetyl-N-1-ethoxycarbonylethylamino)-2-methoxyphenoxy]-n-propyl}-4-phenyl-piperazine are obtained as a pale yellow oil. Yield: 85.5%

IR $\nu_{max}^{liquid}$ (cm$^{-1}$): 1740, 1660, 1245, 1140, 1115, 1035

NMR (CDCl$_3$)δ: 7.4–6.6 (m, 8H, aromatic), 4.96 (q, 1H, J = 7.3 Hz, CH$_3$CH—N$\big\langle$), 4.22 (q, 2H, J=6.9 Hz, —CO$_2$C$\underline{H}_2$CH$_3$), 4.17 (t, 2H, J=7.2 Hz, —OCH$_2$C$\underline{H}_2$—), 3.88 (s, 3H, —OC$\underline{H}_3$), 3.4–3.0 (m, 4H), 2.8–2.4 (m, 6H), 1.86 (s, 3H, C$\underline{H}_3$CON<), 1.31 (t, 3H, J=6.9 Hz, —CO$_2$CH$_2$C$\underline{H}_3$), 1.25 (d, 3H, J = 7.3 Hz, CH$_3$—CH—N$\big\langle$)

Mass m/e: 483 (M+), 203, 175 (base peak)

Hydrochloride:

M.p. 152° C.–154° C. (decomp.) (colorless prisms, recrystallized from a mixture of ethanol and isopropyl ether)

IR $\nu_{max}^{Nujol}$ (cm$^{-1}$): 3400, 2700–2100, 1740, 1660, 1030

EXAMPLE 14

A mixture of 3.78 g of 1-{3-[4-(N-acetyl-N-1-ethoxycarbonylethyl-amino)-2-methoxyphenoxy]-n-propyl}-4-penylpiperazine, 40 ml of 10% hydrochloric acid and 10 ml of conc. hydrochloric acid is refluxed for 2.5 hours. The mixture is allowed to stand at room temperature, and the precipitates are collected by filtration. The precipitates are treated with tetrahydrofuran, whereby 2.7 g of 1-{3-[4-(1-carboxyethylamino)-2-methoxyphenoxy]-n-propyl}-4-phenylpiperazine hydrochloride are obtained as crystalline powder. Yield: 64%

M.p. 180° C.–185° C. (decomp.)

IR $\nu_{max}^{Nujol}$ (cm$^{-1}$): 3350, 2800–2300, 1740, 1145, 1030

NMR (D$_2$O) δ: 7.7–7.0 (m, 8H, aromatic), 3.95 (s, 3H, —OC$\underline{H}_3$), 2.6–2.1 (m, 2H), 1.61 (d, 3H, J = 7.5 Hz, CH$_3$—CH—NH—)

Mass m/e: 413 (M+), 369, 203, 175 (base peak)

EXAMPLE 15

A mixture of 1 g of 1-[3-(4-amino-2-methoxphenoxy)-n-propyl]-4-phenyl-piperazine and 30 ml of ethyl formate is refluxed for 76 hours. After the reaction, the mixture is evaporated to remove an excess of ethyl formate. The residue is dissolved in isopropyl alcohol, and then treated with activated charcoal. 750 mg of 1-[3-(4-formylamino-2-methoxphenoxy)-n-propyl]-4-phenyl-piperazine are thereby obtained as pale yellow granules. Yield: 69.4%

M.p. 113° C.–115° C.

IR $\nu_{max}^{Nujol}$ (cm$^{-1}$): 3295, 1670, 1130, 1040

NMR (CDCl$_3$)δ: 8.61 (s, 1H, H̲CO—NH—), 7.99 (broad s, 1H, HCONH̲—), 7.6–6.8 (m, 8H, aromatic), 4.06 (t, 2H, J=6.7 Hz, —OCH̲$_2$CH$_2$—), 3.81 (s, 3H, —OCH̲$_3$), 3.4–3.0 (m, 4H), 2.8–2.3 (m, 6H), 2.25–1.7 (m, 2H)

Mass m/e: 369 (M+), 203, 175 (base peak)

EXAMPLE 16

A solution of 468 mg of isobutyryl chloride in 3 ml of methylene chloride is added dropwise under ice-cooling to a mixture of one g of 1-[3-(4-amino-2-methoxyphenoxy)-n-propyl]-4-phenyl-piperazine, 586 mg of triethylamine and 40 ml of methylene chloride, and the mixture is stirred at room temperature for one hour. After the reaction, ethylene chloride is added to the mixture, and said mixture is washed with water, dried and then evaporated under reduced pressure to remove the solvent. The residue is recrystallized from ethyl acetate, whereby 1.1 g of 1-[3-(4-isobutyrylamino-2-methoxyphenoxy)-n-propyl]-4-phenyl-piperazine are obtained as colorless needles. Yield: 92%

M.p. 171° C.–172° C.

IR $\nu_{max}^{Nujol}$ (cm$^{-1}$): 3270, 1650, 1135, 1040

NMR (CDCl$_3$)δ: 7.6–6.7 (m, 9H, aromatic and —CO—NH—), 4.07 (t, 2H, J=6.5 Hz, —OCH̲$_2$CH$_2$—), 3.85 (s, 3H, —OCH̲$_3$), 3.4–3.0 (m, 4H), 2.8–2.3 (m, 7H), 2.3–1.8 (m, 2H), 1.23 (d, 6H, J=6.9 Hz, —CH(CH̲$_3$)$_2$)

Mass m/e: 411 (M+), 203, 175 (base peak)

EXAMPLE 17

1.0 g of 1-[3-(4-amino-2-methoxyphenoxy)-n-propyl]-4-phenyl-piperazine, 586 mg of triethylamine, 529 mg of t-butylcarbonyl chloride and 43 ml of methylene chloride are treated in the same manner as described in Example 16. The crude product thus obtained is recrystallized from isopropyl alcohol, whereby 1.09 g of 1-[3-(4-t-butylcarbonylamino-2-methoxyphenoxy)-n-propyl]-4-phenyl-piperazine are obtained as colorless needles. Yield: 87.2%

M.p. 140° C.–142° C.

IR $\nu_{max}^{Nujol}$ (cm$^{-1}$): 3320, 1645, 1140, 1040

NMR (CDCl$_3$)δ: 8.40 (broad s, 1H, —NH—), 7.5–6.6 (m, 8H, aromatic), 4.05 (t, 2H, J=6.5 Hz, —OCH̲$_2$CH$_2$—), 3.82 (s, 3H, —OCH̲$_3$), 3.4–3.0 (m, 4H), 2.8–2.3 (m, 6H), 2.0 (m, 2H), 1.29 (s, 9H, —C(CH̲$_3$)$_3$)

Mass m/e: 425 (M+), 203, 175

EXAMPLE 18

1.0 g of 1-[3-(4-amino-2-methoxyphenoxy)-n-propyl]-4-phenyl-piperazine, 586 mg of triethylamine, 459 mg of cyclopropylcarbonyl chloride and 43 ml of methylene chloride are treated in the same manner as described in Example 16. The crude product thus obtained is recrystallized from ethyl acetate, whereby 910 mg of 1-[3-(4-cyclopropylcarbonylamino-2-methoxyphenoxy)-n-propyl]-4-phenyl-piperazine are obtained as colorless needles. Yield: 75.8%

M.p. 160.5° C.–162.5° C.

IR $\nu_{max}^{Nujol}$ (cm$^{-1}$): 3280, 3050, 1640, 1140, 1040

NMR (CDCl$_3$)δ: 7.9 (broad s, 1H, —NH—), 7.5–6.6 (m, 8H, aromatic), 4.05 (t, 2H, J=6.0 Hz, —OCH̲$_2$CH$_2$—), 3.78 (s, 3H, —OCH̲$_3$), 3.35–3.0 (m, 4H), 2.75–2.3 (m, 6H), 2.0 (m, 2H),

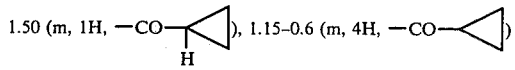

Mass m/e: 409 (M+), 203, 175 (base peak)

EXAMPLE 19

One g of 1-[3-(4-amino-2-methoxyphenoxy)-n-propyl]-4-phenyl-piperazine, 586 mg of triethylamine, 644 mg of cyclohexylcarbonyl chloride and 43 ml of methylene chloride are treated in the same manner as described in Example 16. The crude product thus obtained is recrystallized from ethyl acetate, whereby 1.17 g of 1-[3-(4-cyclohexylcarbonylamino-2-methoxyphenoxy)-n-propyl]-4-phenyl-piperazine are obtained as colorless needles. Yield: 88.6%

M.p. 162° C.–163.5° C.

IR $\nu_{max}^{Nujol}$ (cm$^{-1}$): 3270, 1650, 1140, 1130, 1035

NMR (CDCl$_3$)δ: 7.7–6.8 (m, 9H, aromatic and —NH—), 4.08 (t, 2H, J=6.2 Hz, —OCH̲$_2$CH$_2$—), 3.83 (s, 3H, —OCH̲$_3$), 3.4–3.0 (m, 4H), 2.8–2.35 (m, 7H), 2.3–1.0 (m, 12H)

Mass m/e: 451 (M−), 203, 175

EXAMPLE 20

One gram of 1-[3-(4-amino-2-methoxyphenoxy)-n-propyl]-4-phenyl-piperazine, 586 mg of triethylamine, 494 mg of (2-methyl-1-propenyl)carbonyl chloride and 43 ml of methylene chloride are treated in the same manner as described in Example 16. The crude product thus obtained is recrystallized from ethyl acetate, whereby 596 mg of 1-{3-[4-((2-methyl-1-propenyl)carbonylamino)-2-methoxyphenoxy]-n-propyl}-4-phenyl-piperazine are obtained as colorless granules. Yield: 48%

M.p. 136° C.–138° C.

IR $\nu_{max}^{Nujol}$ (cm$^{-1}$): 3275, 1655, 1140, 1040, 800

NMR (CDCl$_3$)δ: 7.8–6.7 (m, 9H, aromatic and —NH—), 5.03 (broad m, 1H, —CO—CH̲=C<), 4.06 (t, 2H, J=6.5 Hz, —OCH̲$_2$CH$_2$—), 3.81 (s, 3H, —OCH̲$_3$), 3.5–3.0 (m, 4H), 2.9–2.4 (m, 6H), 2.3–1.8 (m, 2H), 1.84 (s, 6H, (CH̲$_3$)$_2$C=CH—)

Mass m/e: 423 (M+), 203, 175 (base peak)

EXAMPLE 21

One gram of 1-[3-(4-amino-2-methoxyphenoxy)-n-propyl]-4-phenyl-piperazine, 439 mg of triethylamine, 479 mg of ethoxycarbonyl chloride and 43 ml of methylene chloride are treated in the same manner as described in Example 16. The crude product thus obtained is recrystallized from isopropyl ether, whereby 960 mg of 1-[3-(4-ethoxycarbonylamino-2-methoxyphenoxy)-n-propyl]-4-phenyl-piperazine are obtained as colorless needles. Yield: 79.2%

M.p. 106.5° C.–107.5° C.

IR $\nu_{max}^{Nujol}$ (cm$^{-1}$): 3330, 1690, 1235, 1140

NMR (CDCl$_3$)δ: 7.45–6.6 (m, 9H, aromatic and —NH—), 4.19 (q, 2H, J=7.0 Hz, —CO$_2$—CH̲$_2$—CH$_3$), 4.05 (t, 2H, J=6.3 Hz, —OCH̲$_2$CH$_2$—), 3.82 (s, 3H, —OCH̲$_3$), 3.4–3.1 (m, 4H), 2.8–2.4 (m, 6H), 2.8–2.4 (m, 2H), 1.29 (t, 3H, J=7.0 Hz, —CO$_2$CH$_2$CH̲$_3$)

Mass m/e: 413 (M+), 368, 203, 175 (base peak)

Methanesulfonate:

M.p. 198°–199° C. (colorless needles, recrystallized from ethanol)

IR$\nu_{max}^{Nujol}$ (cm$^{-1}$): 3260, 2700–2400, 1695, 1230, 1040

Hydrochloride:

M.p. 233° C.–235° C. (decomp.) (colorless granules, recrystallized from methanol)

IR$\nu_{max}^{Nujol}$ (cm$^{-1}$): 3200, 2600–2300, 1705, 1230

EXAMPLE 22

A mixture of 1 g of 1-[3-(4-amino-2-methoxyphenoxy)-n-propyl]-4-phenyl-piperazine, 1.06 g of 2-(t-butoxycarbonylthio)-4,6-dimethylpyrimidine and 15 ml of anhydrous tetrahydrofuran is refluxed for 65 hours. After the reaction, the mixture is evaporated under reduced pressure to remove tetrahydrofuran. Methylene chloride is added to the residue, and the mixture is washed with an aqueous 10% sodium hydroxide solution and water, successively. Said mixture is dried and then evaporated under reduced pressure to remove the solvent. The residue is purified by silica gel chromatography (Solvent; 1.5% methanol/chloroform), and then recrystallized from a mixture of benzene and n-hexane. 1.31 g of 1-[3-(4-t-butoxycarbonylamino-2-methoxyphenoxy)-n-propyl]-4-phenyl-piperazine are thereby obtained as colorless needles. Yield: 85%

M.p. 125° C.–126.5° C.

IR$\nu_{max}^{Nujol}$ (cm$^{-1}$): 3350, 1690, 1160, 1000

NMR (CDCl$_3$)$\delta$: 7.44–6.6 (m, 9H, aromatic and —N$\underline{H}$—), 4.09 (t, 2H, J=6.5 Hz, —OC$\underline{H}_2$CH$_2$—), 3.87 (s, 3H, —OC$\underline{H}_3$), 3.4–3.1 (m, 4H), 2.7–1.5 (m, 6H), 1.51 (s, 9H, —C(C$\underline{H}_3$)$_3$)

Mass m/e: 441 (M$^+$), 175 (base peak)

EXAMPLE 23

45 ml of 0.3% hydrochloric acid and 365 mg of potassium isocyanate are added to a solution of 1.0 g of 1-[3-(4-amino-2-methoxyphenoxy)-n-propyl]-4-phenyl-piperazine in 30 ml of tetrahydrofuran, and mixture is stirred at room temperature for 65 hours. After the reaction, the mixture is evaporated under reduced pressure to remove tetrahydrofuran. The residue is ice-cooled, and the crystalline precipitates are collected by filtration. The precipitates thus obtained are recrystallized from a mixture of methanol and ethanol. 980 mg of 1-[3-(4-carbamonylamino-2-methoxyphenoxy)-n-propyl]-4-phenyl-piperazine are thereby obtained as colorless needles. Yield: 83%

M.p. 184° C.–185° C.

IR$\nu_{max}^{Nujol}$ (cm$^{-1}$): 3460, 3340, 3260, 1660, 1230, 1140, 1000

NMR (DMSO-d$_6$)$\delta$: 8.46 (broad s, 1H, H$_2$HCON$\underline{H}$—, disappeared by D2O), 7.5–6.6 (m, 8H, aromatic), 5.75 (broad s, 2H, $\underline{H}_2$NCONH—, disappeared by D2O), 3.94 (t, 2H, J=6.0 Hz, —OC$\underline{H}_2$C-H$_2$—), 3.74 (s, 3H, —OC$\underline{H}_3$), 3.4–2.9 (m, 4H), 2.9–2.3 (m, 6H), 2.25–1.5 (m, 2H).

Mass m/e: 367 (M$^+$-17), 175 (base peak)

EXAMPLE 24

A mixture of 2.0 g of 1-[3-(4-amino-2-methoxyphenoxy)-n-propyl]-4-phenyl-piperazine and 820 mg of trimethyl phosphate is stirred at 200° C. for 50 minutes. After the reaction mixture is cooled, an aqueous 10% sodium hydroxide solution is added thereto, and the aqueous mixture is extracted with chloroform. The extract is washed with water, dried and then evaporated under reduced pressure to remove the solvent. The residue is purified by silica gel chromatography (Solvent; 1% methanol/chloroform), whereby 640 mg of 1[3-(4-dimethylamino-2-methoxyphenoxy)-n-propyl]-4-phenyl-piperazine are obtained as a pale yellow oil. Yield: 29%

IR$\nu_{max}^{liquid}$ (cm$^{-1}$): 1670, 1600, 1140, 1030

NMR (CDCl$_3$)$\delta$: 7.5–6.6 (m, 7H, aromatic), 6.5–6.1 (m, 1H, aromatic), 4.03 (t, 2H, J=6.1Hz, —OC$\underline{H}_2$C-H$_2$—), 3.86 (s, 3H, —OC$\underline{H}_3$), 3.4–3.0 (m, 4H), 2.88 (s, 6H, —N(C$\underline{H}_3$)$_2$), 2.7–2.3 (m, 6H), 2.3–1.6 (m, 2H).

Mass m/e: 369 (M$^+$), 203, 175 (base peak)

Hydrochloride:

M.p. 240° C.–244° C. (decomp.) (pale brown needles, recrystallized from methanol)

IR$\nu_{max}^{Nujol}$ (cm$^{-1}$): 2700–2200, 1600, 1140, 1010

EXAMPLE 25

1.05 g of triethylamine are added to a solution of 745 mg of 1-[3-(4-amino-2-methoxyphenoxy)-n-propyl]-4-phenyl-piperazine in 15 ml of chloroform, and 1.13 g of methanesulfonyl chloride are added at a temperature below 10° C. thereto. The mixture is stirred at room temperature for 48 hours. Chloroform is added to the reaction mixture, and said mixture is washed with water, dried and then evaporated under reduced pressure to remove the solvent. The residue is purified by silica gel chromatography (Solvent; 1% methanol/chloroform), whereby 840 mg of 1-{3-[4-di(methylsulfonyl)amino-2-methoxyphenoxy]-n-propyl}-4-phenyl-piperazine are obtained. Yield: 77.5%

M.p. 157.5° C.–158° C. (colorless needles, recrystallized from benzene)

IR$\nu_{max}^{Nujol}$ (cm$^{-1}$): 1600, 1370, 1155, 1000

NMR (CDCl$_3$)$\delta$: 7.6–6.8 (m, 9H, aromatic and 1/5 C$_6$H$_6$), 4.16 (t, 2H, J=6.2 Hz, —OC$\underline{H}_2$—C$\underline{H}_2$—), 3.86 (s, 3H, —OC$\underline{H}_3$), 3.40 (s, 6H, (C$\underline{H}_3$SO$_2$)$_2$N—), 3.4–3.1 (m, 4H), 2.9–2.4 (m, 6H), 2.3–1.8 (m, 2H)

Mass m/e: 497 (M$^+$), 419, 203, 175 (base peak)

Analysis calculated for C$_{22}$H$_{31}$N$_3$O$_6$S$_2$.1/5 C$_6$H$_6$: C, 54.29; H, 6.32; N, 8.19, S, 12.49. Found: C, 54.29; H, 6.47; N, 8.20; S, 12.45.

The remains contained in the column is further eluted with 2% methanol/chloroform, whereby 130 mg of 1[3-(4-methylsulfonylamino-2-methoxyphenoxy)-n-propyl]-4-phenyl-piperazine are obtained. Yield: 14.2%

M.p. 130° C.–131° C. (colorless needles, recrystallized from benzene)

IR$\nu_{max}^{Nujol}$ (cm$^{-1}$): 3270, 1600, 1335, 1155

NMR (CDCl$_3$)$\delta$: 7.6–6.7 (m, 8H, aromatic), 6.5–5.7 (broad m, 1H, —N$\underline{H}$—), 4.10 (t, 2H, J=6.2 Hz, —OC$\underline{H}_2$—CH$_2$—), 3.85 (s, 3H, —OC$\underline{H}_3$), 3.6–3.1 (m, 4H), 2.94 (s, 3H, C$\underline{H}_3$SO$_2$NH—), 2.9–2.45 (m, 6H), 2.4–1.8 (m, 2H)

Mass m/e: 419 (M$^+$), 203, 175

EXAMPLE 26

1.3 g of 1-(4-acetamido-2-methoxyphenoxy)-3-(p-toluenesulfonyloxy)-n-propane, 690 mg of 4-(3-chlorophenyl)piperazine, 355 mg of triethylamine and 40 ml of ethanol are treated in the same manner as described in Example 1. The crude product thus obtained is recrystallized from isopropyl alcohol, whereby 1.27 g of 1-[3-(4-acetamido-2-methoxyphenoxy)-n-propyl]-4-(3-chlorophenyl)-piperazine are obtained as colorless needles. Yield: 92%

M.p. 138° C.–139° C.

IR$\nu_{max}^{Nujol}$ (cm$^{-1}$): 3280, 1655, 1140, 1040

NMR (CDCl$_3$)$\delta$: 7.79 (broad s, 1H, —N$\underline{H}$—), 7.5–6.6 (m, 7H, aromatic), 4.10 (t, 2H, J=6.1 Hz, —OC$\underline{H}_2$C-

H$_2$—), 3.85 (s, 3H, —OC$\underline{H}_3$), 3.4–3.0 (m, 4H), 2.8–2.3 (m, 6H), 2.3–1.8 (m, 2H), 2.14 (s, 3H, C$\underline{H}_3$CONH—)

Mass m/e: 419, 417 (M+), 211, 209 (base peak)

EXAMPLE 27

1.3 g of 1-(4-acetamido-2-methoxyphenoxy)-3-(p-toluenesulfonyloxy-n-propane, 620 mg of 4-(2-methylphenyl)piperazine, 355 mg of triethylamine and 40 ml of ethanol are treated in the same manner as described in Example 1. The crude product thus obtained is recrystallized from acetone, whereby 1.31 g of 1[3-(4-acetamido-2-methoxyphenoxy)-n-propyl]-4-(2-methylphenyl)-piperazine are obtained as colorless prisms. Yield: 92%

M.p. 109° C.–110° C.

IR$\nu_{max}^{Nujol}$ (cm$^{-1}$): 3275, 1655, 1135, 1040

NMR (CDCl$_3$)δ: 7.82 (broad s, 1H, —N$\underline{H}$—), 7.5–6.7 (m, 7H, aromatic), 4.08 (t, 2H, J=6.4 Hz, —OC$\underline{H}_2$C-H$_2$—), 3.82 (s, 3H, —OC$\underline{H}_3$), 3.15–2.8 (m, 4H), 2.8–2.4 (m, 6H), 2.30 s, 3H, —Ph—C$\underline{H}_3$), 2.3–1.8 (m, 2H), 2.12 (s, 3H, C$\underline{H}_3$CONH-)

Mass m/e: 397 (M+), 189 (base peak)

EXAMPLE 28

3 g of 1-(4-acetamido-2-methoxyphenoxy)-4-(p-toluenesulfonyloxy)-n-butane, 1.78 g of 4-phenylpiperazine, 1.1 g of triethylamine and 50 ml of ethanol are treated in the same manner as described in Example 1. The crude product thus obtained is recrystallized from benzene, whereby 2.71 g of 1-[4-(4-acetamido-2-methoxyphenoxy)-n-butyl]-4-phenylpiperazine are obtained as colorless needles. Yield: 92.5%.

M.p. 128° C.–129° C.

IR$\nu_{max}^{Nujol}$ (cm$^{-1}$): 3250, 1650, 1135, 1040

NMR (CDCl$_3$)δ: 7.45 (broad s, 1H, —N$\underline{H}$—), 7.1–6.3 (m, 8H, aromatic), 3.78 (t, 2H, J=5.2 Hz, —OC$\underline{H}_2$C-H$_2$—), 3.59 (s, 3H, —OC$\underline{H}_3$), 3.2–2.8 (m, 4H), 2.65–2.1 (m, 6H), 1.97 (s, 3H, C$\underline{H}_3$CONH—), 1.9–1.3 (m, 4H)

Mass m/e: 397 (M+), 217 (base peak), 175

Methanesulfonate:

M.p. 184° C.–185° C. (colorless plates, recrystallized from ethanol

IR$\nu_{max}^{Nujol}$ (cm$^{-1}$): 3400, 3280, 2800–2300, 1670, 1165, 1145, 1045

EXAMPLE 29

1.0 g of 1-[3-(4-amino-2-methoxyphenoxy)-n-propyl]-4-phenyl-piperazine, 586 mg of triethylamine, 529 mg of n-pentanoyl chloride and 43 ml of methylene chloride are treated in the same manner as described in Example 16. The crude product thus obtained is recrystallized from isopropyl alcohol, whereby 840 mg of 1-[3-(4-pentanamido-2-methoxyphenoxy)-n-propyl]-4-phenyl-piperazine are obtained as colorless needles. Yield: 67%

M.p. 117° C.–118° C.

IR$\nu_{max}^{Nujol}$ (cm$^{-1}$): 3300, 1650, 1140, 1040, 1020

NMR (CDCl$_3$)δ: 7.65 (broad s, 1H, —N$\underline{H}$—), 7.5–6.7 (m, 8H, aromatic), 4.03 (t, 2H, J=6.5 Hz, —OC$\underline{H}_2$C-H$_2$—), 3.79 (s, 3H, —OC$\underline{H}_3$), 3.4–3.0 (m, 4H), 2.8–1.0 (m, 14H), 0.91 (broad t, 3H, J=6.5 Hz, C$\underline{H}_3$CH$_2$—)

Mass m/e: 425 (M+), 203, 175

EXAMPLE 30

10.13 g of 4-acetamido-2-methoxyphenol, 2.24 g of sodium hydroxide, 12.14 g of 1-(3- chloro-n-propyl)-4-phenylpiperazine and 300 ml of anhydrous dimethylsulfoxide are treated in the same manner as described in Example 10. The crude product thus obtained is recrystallized from a mixture of benzene and ethyl acetate, whereby 17.2 g of 1-[3-(4-acetamido-2-methoxyphenoxy)-n-propyl]-4-phenyl-piperazine are obtained. Yield: 88%

The physico-chemical properties of the product are identical with those of the sample obtained in Example 9.

EXAMPLE 31

1.0 g of 4-ethoxycarbonylamino-2-methoxyphenol, 200 mg of sodium hydroxide, 1.2 g of 1-(3-chloro-n-propyl)-4-(3-methylphenyl)-piperazine and 30 ml of anhydrous dimethylsulfoxide are treated in the same manner as described in Example 10. The crude product thus obtained is recrystallized from isopropyl ether, whereby 1.26 g of 1-[3-(4-ethoxycarbonylamino-2-methoxyphenoxy)-n-propyl]-4-(3-methylphenyl)-piperazine are obtained as colorless needles. Yield: 63%

M.p. 112° C.–113° C.

IR $\nu_{max}^{Nujol}$ (cm$^{-1}$): 3340, 1695, 1530, 1240, 1140

NMR (CDCl$_3$)δ: 7.4–6.3 (m, 8H, aromatic and —N$\underline{H}$—), 4.20 (q, 2H, J=7.0 Hz, —COOC$\underline{H}_2$CH$_3$), 4.05 (t, 2H, J=6.1 Hz, —O—C$\underline{H}_2$CH$_2$—), 3.85 (s, 3H, —OC$\underline{H}_3$), 3.4–3.0 (m, 4H), 2.8–2.4 (m, 6H), 2.30 (s, 3H, —C$\underline{H}_3$), 2.3–1.6 (m, 2H), 1.29 (t, 3H, J=7.0 Hz, —COOCH$_2$C$\underline{H}_3$)

Mass m/e: 427 (M+), 381, 217, 189 (base peak) Methanesulfonate:

M.p. 182° C.–183° C. (colorless needles, recrystallized from ethanol)

IR $\nu_{max}^{Nujol}$ (cm$^{-1}$): 3250, 2800–2300, 1720, 1230, 1170, 1040

EXAMPLE 32

1.0 g of 4-ethoxycarbonylamino-2-methoxyphenol, 200 mg of sodium hydroxide, 1.3 g of 1-(3-chloro-n-propyl)-4-(3-chlorophenyl)-piperazine and 30 ml of anhydrous dimethylsulfoxide are treated in the same manner as described in Example 10. The crude product thus obtained is recrystallized from a mixture of isopropyl ether and benzene, whereby 1.85 g of 1-[3-(4-ethoxycarbonylamino-2-methoxyphenoxy)-n-propyl]-4-(3-chlorophenyl)-piperazine are obtained as colorless needles. Yield: 87.5%

M.p. 109° C.–110° C.

IR $\nu_{Max}^{Nujol}$(cm$^{-1}$): 3350, 1695, 1235, 1140

NMR (CDCl$_3$)δ: 7.4–6.4 (m, 8H, aromatic and —N$\underline{H}$—), 4.22 (q, 2H, J=7.0 Hz, —COOC$\underline{H}_2$CH$_3$) 4.07 (t, 2H, J=6.3 Hz, —O—C$\underline{H}_2$CH$_2$), 3.85 (s, 3H, —OC$\underline{H}_3$), 3.4–3.0 (m, 4H), 2.8–2.3 (m, 6H), 2.3–1.6 (m, 2H), 1.31 (t, 3H, J=7.0 Hz, —COOCH$_2$C$\underline{H}_3$)

Mass m/e: 449, 447 (M+), 401, 239, 237, 211, 209 (base peak)

Methanesulfonate:

M.p. 163° C.–164° C. (colorless granules, recrystallized from ethanol)

IR $\nu_{max}^{Nujol}$ (cm$^{-1}$): 3260, 2750–2400, 1715, 1220, 1165, 1045

EXAMPLE 33

1.0 g of 4-ethoxycarbonylamino-2-methoxyphenol, 200 mg of sodium hydroxide, 1.25 g of 1-(3-chloro-n-propyl)-4-(3-fluorophenyl)-piperazine and 30 ml of anhydrous dimethylsulfoxide are treated in the same manner as described in Example 10. The crude product thus obtained is recrystallized from a mixture of isopropyl ether and benzene, whereby 1.79 g of 1-[3-(4-ethoxycarbonylamino-2-methoxyphenoxy)-n-propyl]-4-(3-fluorophenyl)-piperazine are obtained as colorless needles. Yield: 87.6%

M.p. 114° C.–115° C.

IR $\nu_{max}^{Nujol}$ (cm$^{-1}$): 3340, 1695, 1240, 1140

NMR (CDCl$_3$)δ: 7.4–6.3 (m, 8H, aromatic and —N$\underline{H}$—), 4.23 (q, 2H, J=7.0 Hz, —COOCH$_2$CH$_3$) 4.07 (t, 2H, J=6.3 Hz, —O—CH$_2$CH$_2$—), 3.86 (s, 3H, —OC$\underline{H}_3$), 3.4–3.1 (m, 4H), 2.8–2.4 (m, 6H), 2.3–1.7 (m, 2H), 1.30 (t, 3H, J=7.0 Hz, —COOCH$_2$C$\underline{H}_3$)

Mass m/e: 431 (M$^+$), 385, 221, 193 (base peak)
Methanesulfonate:

M.p. 188°–189° C. (colorless needles, recrystallized from ethanol)

IR $\nu_{max}^{Nujol}$ (cm$^{-1}$): 3270, 2750–2400, 1710, 1220, 1175, 1160, 1040

EXAMPLE 34

1.07 g of 4-(2-fluorophenyl)piperazine and 1.5 ml of triethylamine are added to a solution of 1.5 g of 2-(4-acetamido-2-methoxyphenoxy)-1-(p-toluenesulfonyloxy)ethane in 10 ml of anhydrous dimethylformamide, and the mixture is stirred at 100° C. for 6 hours. After the reaction, the mixture is poured into ice-water, and the aqueous mixture is extracted with chloroform. The extract is washed with water and an aqueous saturated sodium chloride solution, successively. Said extract is dried and then evaporated under reduced pressure to remove the solvent. The residue is purified by silica gel chromatography (Solvent; 2% methoanol/chloroform), and then recrystallized from a mixture of ethyl acetate and n-hexane. 1.3 g of 1-[2-(4-acetamido-2-methoxyphenoxy)ethyl]-4-(2-fluorophenyl)-piperazine are thereby obtained as colorless scales. Yield: 85%

M.p. 118° C.–119° C.

IR $\nu_{max}^{Nujol}$ (cm$^{-1}$): 3250, 3200, 1655, 1140

NMR (CDCl$_3$)δ: 8.00 (broad s, 1H, —N$\underline{H}$—), 7.4–6.45 (m, 7H, aromatic), 4.11 (t, 2H, J=6.0 Hz, —OC$\underline{H}_2$CH$_2$—), 3.75 (s, 3H, —OC$\underline{H}_3$), 3.45–2.45 (m, 10H), 2.10 (s, 3H, C$\underline{H}_3$CONH—)

Mass m/e: 387 (M$^+$), 207, 193 (base peak)
Hydrochloride:

M.p. 178.5°–179.5° C. (colorless needles, recrystallized from a mixture of isopropyl alcohol and isopropyl ether)

IR $\nu_{max}^{Nujol}$ (cm$^{-1}$): 3250, 2700–2300, 1670, 1140, 1030, 1010

EXAMPLE 35

1.5 g of 6-(4-acetamido-2-methoxyphenoxy)-1-(p-toluenesulfonyloxy)-n-hexane, 670 mg of 4-phenylpiperazine, 520 mg of triethylamine and 20 ml of anhydrous dimethylformamide are treated in the same manner as described in Example 34. The crude product thus obtained is recrystallized from ethyl acetate, whereby 1.07 g of 1-[6-(4-acetamido-2-methoxyphenoxy)-n-hexyl]-4-phenyl-piperazine are obtained as colorless scales. Yield: 73%

M.p. 103° C.–104° C.

IR $\nu_{max}^{Nujol}$ (cm$^{-1}$): 3250, 3200, 1660, 1140 1030

NMR (CDCl$_3$)δ: 7.7 (broad s, 1H, —N$\underline{H}$—), 7.45–6.5 (m, 8H, aromatic), 3.97 (broad t, 2H, J=6 Hz, —OC$\underline{H}_2$CH$_2$—), 3.78 (s, 3H, —OC$\underline{H}_3$), 3.5–2.95 (m, 4H), 2.8–1.0 (m, 14H), 2.10 (s, 3H, C$\underline{H}_3$CONH—)

Mass m/e: 425 (M$^+$), 175 (base peak)
Hydrochloride:

M.p. 183°–185° C. (decomp.) (colorless needles, recrystallized from a mixture of methanol and isopropyl alcohol)

IR $\nu_{max}^{Nujol}$ (cm$^{-1}$): 3250, 2700–2400, 1680, 1130, 1030

EXAMPLE 36

2 g of 1-[3-(4-acetamido-2-methoxyphenoxy)-n-propyl]-4-phenyl-piperazine, 232 mg of 65% sodium hydride, 940 mg of 3-methyl-2-butenyl bromide and 60 ml of anhydrous dimethylformamide are treated in the same manner as described in Example 13. 1.78 g of 1-{3-[4-(N-acetyl-N-(3-methyl-2-butenyl)-amino)-2-methoxyphenoxy]-n-propyl}-4-phenyl-piperazine are thereby obtained as a pale yellow oil. Yield: 86.3%

IR $\nu_{max}^{liq.}$ (cm$^{-1}$): 1655, 1240, 1035

NMR (CDCl$_3$)δ: 7.4–6.5 (m, 8H, aromatic), 5.18 (broad d, 1H, J=7.5 Hz, —CH$_2$—C$\underline{H}$=C<), 4.24 (d, 2H, J = 7.5 Hz, —N—CH$_2$—CH=), 4.10 (t, 2H, J=6 Hz, —OC$\underline{H}_2$CH$_2$—), 3.84 (s, 3H, —OC$\underline{H}_3$), 3.4–3.0 (m, 4H), 2.8–2.4 (m, 6H), 2.3–1.8 (m, 2H), 1.85 (s, 3H, C$\underline{H}_3$CON<), 1.68 and 1.43 (s, 3H and s, 3H, (C$\underline{H}_3$)$_2$C=CH—)

Mass m/e: 451 (M$^+$, base peak), 203, 175

EXAMPLE 37

1.6 g of 1-{3-[4-(N-acetyl-N-(3-methyl-2-butenyl)amino)-2-methoxyphenoxy]-n-propyl}-4-phenyl-piperazine, 15 ml of 10% hydrochloric acid and 3 ml of conc. hydrochloric acid are treated in the same manner as described in Example 14. The crude product thus obtained is recrystallized from ethanol, whereby 1.35 g of 1-{3-[4-(3-methyl-2-butenylamino)-2-methoxyphenoxy]-n-propyl}-4-phenyl-piperazine hydrochloride are obtained as colorless prisms. Yield: 75.3%

M.p. 218° C.–220° C. (decomp.)

IR $\nu_{max}^{Nujol}$ (cm$^{-1}$): 3440, 3380, 2800–2400, 1640

NMR (CDCl$_3$)δ: 7.6–6.7 (m, 8H, aromatic), 4.2 (broad, 2H) 3.77 (s, 3H, —OC$\underline{H}_3$), 1.30 (broad s, 6H, (C$\underline{H}_3$)$_2$C=CH—)

Mass m/e: 409 (M$^+$), 203 (base peak), 175

EXAMPLE 38

1 g of 1-[3-(4-amino-2-methoxyphenoxy)-n-propyl]-4-phenylpiperazine and 878 mg of triethylamine are dissolved in 40 ml of methylene chloride, and a solution of 1.84 g of trifluoroacetic anhydride in 3 ml of methylene chloride is added dropwise at a temperature below 10° C. thereto. The mixture is stirred at room temperature for 4 hours. Then, methylene chloride is added to the reaction mixture, and said mixture is washed with water, dried and then evaporated under reduced pressure to remove the solvent. The residue thus obtained is purified by silica gel chromatography (Solvent; 1% methanol/chloroform), whereby 787 mg of 1-[3-(4-trifluoroacetamido-2-methoxyphenoxy)-n-propyl]-4-phenyl-piperazine are obtained. Yield: 61.5%

M.p. 144.5° C.–145.5° C.

IR $\nu_{max}^{nujol}$ (cm$^{-1}$): 3290, 1700, 1150, 1140, 1035

NMR (CDCl$_3$)δ: 8.26 (broad, 1H, —N$\underline{H}$—), 7.5–6.8 (m, 8H, aromatic), 4.10 (t, 2H, J=6.5 Hz, —OC$\underline{H}_2$C$\underline{H}_2$—), 3.83 (s, 3H, —OC$\underline{H}_3$), 3.4–3.1 (m, 4H), 2.9–2.4 (m, 6H), 2.4–1.9 (m, 2H)

Mass m/e: 437 (M$^+$), 203, 175 (base peak)

EXAMPLE 39

1 g of 1-[3-(4-amino-2-methoxyphenoxy)-n-propyl]-4-phenylpiperazine, 586 mg of triethylamine, 714 mg of n-octanoyl chloride and 43 ml of methylene chloride are treated in the same manner as described in Example 16. The crude product thus obtained is recrystallized from ethyl acetate, whereby 1.08 g of 1-[3-(4-n-octanamido-2-methoxyphenoxy)-n-propyl]-4-phenyl-piperazine are obtained as colorless needles. Yield: 78.8%

M.p. 124° C.–126° C.

IR $\nu_{max}^{nujol}$ (cm$^{-1}$): 3280, 1650, 1135, 1040, 1020

NMR (CDCl$_3$)$\delta$: 7.7–6.7 (m, 9H, aromatic and —N$\underline{H}$—), 4.07 (t, 2H, J=6.3 Hz, —OC$\underline{H}_2$CH$_2$—), 3.83 (s, 3H, —OC$\underline{H}_3$), 3.4–3.0 (m, 4H, 2.8–1.0 (m, 20H), 0.88 (broad t, 3H, —CH$_2$C$\underline{H}_3$)

Mass m/e: 467 (M$^+$), 203, 175

EXAMPLE 40

2.0 g of 1-[3-(4-amino-2-methoxyphenoxy)-n-propyl]-4-phenyl-piperazine, 800 mg of triethylamine, 1.0 g of 3-methoxycarbonyl-propionyl chloride and 30 ml of methylene chloride are treated in the same manner as described in Example 16. The crude product thus obtained is recrystallized from ethyl acetate, whereby 2.51 g of 1-{3-[4-(3-methoxycarbonyl-propionamido)-2-methoxyphenoxy]-n-propyl}-4-phenyl-piperazine are obtained as colorless needles. Yield: 94%

M.p. 134° C.–136° C.

IR $\nu_{max}^{Nujol}$ (cm$^{-1}$): 3360, 1725, 1670, 1140

NMR (CDCl$_3$)$\delta$: 7.90 (broad s, 1H, —N$\underline{H}$—), 7.6–6.65 (m, 8H, aromatic), 4.04 (t, 2H, J=6.3 Hz, —OC$\underline{H}_2$CH$_2$—), 3.79 (s, 3H, —OC$\underline{H}_3$), 3.66 (s, 3H, —CO$_2$C$\underline{H}_3$), 3.45–3.0 (m, 4H), 2.9–2.3 (m, 10H), 2.3–1.8 (m, 2H)

Mass m/e: 455 (M$^+$), 203, 175 (base peak)

EXAMPLE 41

260 mg of methyl isocyanate are added to a solution of 1.0 g of 1-[3-(4-amino-2-methoxyphenoxy)-n-propyl]-4-phenylpiperazine in 60 ml of anhydrous benzene, and the mixture is stirred at room temperature for 95 hours. The crystalline precipitates are collected by filtration, and then recrystallized from isopropyl alcohol. 1.11 g of 1-{3-[4-(3-methylureido)-2-methoxyphenoxy]-n-propyl}-4-phenyl-piperazine are thereby obtained as colorless needles. Yield: 93%

M.p. 167° C.–169° C.

IR $\nu_{max}^{Nujol}$ (cm$^{-1}$): 3360, 3300, 1650, 1250, 1145, 1040

NMR (CDCl$_3$+DMSO-d$_6$)$\delta$: 8.01 (broad s, 1H, CH$_3$NHCON$\underline{H}$, disappeared by D2O), 7.5–6.56 (m, 8H, aromatic), 6.0–5.5 (m, 1H, CH$_3$N$\underline{H}$CONH—, disappeared by D2O), 4.05 (t, 2H, J=6.4 Hz, —OC$\underline{H}_2$CH$_2$—); 3.84 (s, 3H, —OC$\underline{H}_3$), 3.5–3.0 (m, 4H), 2.77 (d, 3H, J=5.2 Hz, C$\underline{H}_3$NHCO—), D2O), 2.7–2.35 (m, 6H), 2.3–1.7 (m, 2H)

Mass m/e: 398 (M$^+$), 203, 175 (base peak)

EXAMPLE 42

800 mg of 1-[3-(4-amino-2-methoxyphenoxy)-n-propyl]-4-phenyl-piperazine, 310 mg of phenyl isocyanate and 60 ml of anhydrous benzene are treated in the same manner as described in Example 41. The crude product thus obtained is recrystallized from ethyl acetate, whereby 970 mg of 1-{3-[4-(3-phenylureido)-2-methoxyphenoxy]-n-propyl}-4-phenylpiperazine are obtained as colorless needles. Yield: 89.8%

M.p. 165.5° C.–166.5° C.

IR $\nu_{max}^{Nujol}$ (cm$^{-1}$): 3310, 1650, 1610, 1240, 1140, 1030

NMR (CDCl$_3$)$\delta$: 7.9–6.75 (m, 15H, aromatic and Ph—NHCON$\underline{H}$—), 4.03 (t, 2H, J=6.0 Hz, —OC$\underline{H}_2$CH$_2$—), 3.72 (s, 3H, —OC$\underline{H}_3$), 3.4–3.0 (m, 4H), 2.8–2.35 (m, 6H), 2.3–1.7 (m, 2H)

Mass m/e: 460 (M$^+$), 203, 175 (base peak)

EXAMPLE 43

A mixture of 20 g of 1-{3-[4-(3-methoxycarbonyl-propionamido)-2-methoxyphenoxy]-n-propyl}-4-phenyl-piperazine and 2 ml of xylene is stirred at 150° C. for 20 hours. Then, chloroform is added to the reaction mixture, and said mixture is treated with activated charcoal and then evaporated under reduced pressure to remove the solvent. The residue is purified by silica gel chromatography (Solvent: 1% methanol/chloroform), and then recrystallized from ethyl acetate. 910 mg of 1-[3-(4-succinimido-2-methoxyphenoxy)-n-propyl]-4-phenyl-piperazine are obtained as colorless needles. Yield: 54%

M.p. 165.5° C.–167° C.

IR $\nu_{max}^{Nujol}$ (cm$^{-1}$): 1710, 1690, 1040

NMR (CDCl$_3$)$\delta$: 7.5–6.6 (m, 8H, aromatic), 4.11 (t, 2H, J=6.5 Hz, —OC$\underline{H}_2$CH$_2$—), 3.84 (s, 3H, —OC$\underline{H}_3$), 3.5–3.1 (m, 4H), 2.81 (s, 4H, succinyl), 3.0–2.4 (m, 6H), 2.4–1.8 (m, 2H) Mass m/e: 423 (M$^+$), 203, 175 (base peak)

EXAMPLE 44

2.54 g of 4-acetamido-2-methoxyphenol, 585 mg of sodium hydroxide, 2.62 g of 1-(2-chloroethyl)-4-phenyl-piperazine and 60 ml of anhydrous dimethylsulfoxide are treated in the same manner as described in Example 10. The crude product thus obtained is recrystallized from benzene, whereby 3.48 g of 1-[2-(4-acetamido-2-methoxyphenoxy)ethyl]-4-phenyl-piperazine are obtained as colorless prisms. Yield: 67.6%

M.p. 134° C.–135° C.

IR $\nu_{max}^{Nujol}$ (cm$^{-1}$): 3200, 1645, 1600, 1150, 1140, 1030

NMR (CDCl$_3$)$\delta$: 7.96 (broad, 1H, —NH—, disappeared by D2O), 7.5–6.5 (m, 8H, aromatic), 4.14 (t, 2H, J=5.9 Hz, —OC$\underline{H}_2$CH$_2$—), 3.78 (s, 3H, —OC$\underline{H}_3$), 3.4–3.0 (m, 4H), 3.0–2.4 (m, 6H), 2.10 (s, 3H, C$\underline{H}_3$CONH—)

Mass m/e: 369 (M$^+$), 189, 175 (base peak)

Methanesulfonate:

M.p. 147° C.–148° C. (colorless prisms, recrystallized from isopropyl alcohol)

IR $\nu_{max}^{Nujol}$ (cm$^{-1}$): 3300–3000, 2800–2400, 1665, 1600, 1165, 1130, 1040

PREPARATION 1

(1) 13.4 g of 4-acetamido-2-methoxyphenol are dissolved in 80 ml of dimethylsulfoxide under nitrogen atmosphere, and 2.96 g of powdery sodium hydroxide are added thereto. The mixture is stirred at 50° C. to 55° C. for 3 hours. A solution of 10 g of 2-chloro-1-(tetrahydropyran-2-yl-oxy)ethane in 20 ml of dimethylsulfoxide is added dropwise to the mixture, and said mixture is stirred at 100° C. for one hour. After the reaction, the mixture is poured into ice-water, and the aqueous mixture is extracted with ethyl acetate. The extract is washed with water and an aqueous saturated sodium chloride solution, successively. Said extract is dried and then evaporated under reduced pressure to remove the solvent. The residue is recrystallized from a mixture of ethyl acetate and n-hexane, whereby 15.5 g of 1-(4-acetamido-2-methoxyphenoxy)-2-(tetrahydropyran-2-yl-oxy)ethane are obtained as colorless needles. Yield: 82.5%

M.p. 88° C.–90° C.

(2) 15.5 g of the product obtained in paragraph (1) are dissolved in a mixture of 70 ml of ethanol and 140 ml of water, and 0.1 ml of conc. hydrochloric acid is added thereto. The mixture is stirred at room temperature for 2 days. After the reaction, the mixture is evaporated under reduced pressure to remove ethanol. The residue is cooled, and the crystalline precipitates are collected and then recrystallized from ethanol. 9.43 g of 1-(4-acetamido-2-methoxyphenoxy)-2-hydroxy-ethane are thereby obtained as colorless prisms. Yield: 84%

M.p. 157° C.–159° C.

(3) 5 g of the product obtained in paragraph (2) are dissolved in 120 ml of pyridine, and a solution of 5 g of p-toluenesulfonyl chloride in 30 ml of pyridine is added dropwise at 0° C. to 5° C. thereto. The mixture is allowed to stand under ice-cooling for 5 days. Then, the mixture is poured into ice-water, and the aqueous mixture is extracted with ethyl acetate. The extract is washed with 10% hydrochloric acid and water, successively. Said extract is dried and then evaporated under reduced pressure to remove the solvent. The residue is recrystallized from a mixture of ethyl acetate and n-hexane, whereby 5.9 g of 1-(4-acetamido-2-methoxyphenoxy)-2-(p-toluenesulfonyloxy)ethane are obtained as colorless needles. Yield: 70%

M.p. 106° C.–107.5° C.

PREPARATION 2

(1-a) 33 g of ethyl acrylate are added to 6 g of 4-acetamido-2-methoxyphenol, and 0.5 ml of 40% benzyltrimethylammonium hydroxide/methanol are added thereto. The mixture is stirred at 100° C. to 110° C. for 6 days. After the reaction, the mixture is concentrated under reduced pressure to remove an excess of ethyl acrylate. Chloroform is added to the residue, and the chloroform solution is washed with 2% hydrochloric acid, water and an aqueous saturated sodium chloride solution. Said chloroform solution is dried and then evaporated under reduced pressure to remove the solvent. The residue is purified by silica gel chromatography (Solvent; 2% methanol/chloroform), whereby 1.47 g of 1-(4-acetamido-2-methoxyphenoxy)-2-(ethoxycarbonyl)ethane are obtained.

M.p. 103° C.–104° C. (colorless needles, recrystallized from benzene)

(1-b) 138 g of ethyl acrylate are added to 25 g of 4-acetamido-2-methoxyphenol, and 250 mg of powdery sodium hydroxide are added thereto. The mixture is refluxed for 6 days, and then concentrated under reduced pressure to remove an excess of ethyl acrylate. Chloroform is added to the residue, and the chloroform solution is washed with an aqueous saturated sodium chloride solution, dried and then evaporated under reduced pressure to remove the solvent. The residue is purified by silica gel chromatography (Solvent; 2% methanol/chloroform), whereby 8.55 g of 1-(4-acetamido-2-methoxyphenoxy)-2-(ethoxycarbonyl)ethane are obtained. Yield: 22%

The physico-chemical properties of the product are identical with the sample obtained in paragraph (1-a).

(2) A solution of 21 g of 1-(4-acetamido-2-methoxyphenoxy)-2-(ethoxycarbonyl)ethane in 300 ml of anhydrous tetrahydrofuran is added dropwise at a temperature below 0° C. under stirring to a suspension of 5.55 g of lithium aluminum hydride in 500 ml of tetrahydrofuran, and the mixture is stirred at the same temperature for 3 hours. After decomposing an excess of lithium aluminum hydride, insoluble materials are removed by filtration. The filtrate is concentrated under reduced pressure to remove the solvent. The residue is recrystallized from a mixture of acetone and ethyl acetate, whereby 14.47 g of 1-(4-acetamido-2-methoxyphenoxy)-3-hydroxy-n-propane are obtained as colorless needles. Yield: 81%

M.p. 121° C.–122° C.

(3) 14.47 g of 1-(4-acetamido-2-methoxyphenoxy)-3-hydroxy-n-propane, 17.5 g of p-toluenesulfonyl chloride and 130 ml of pyridine are treated in the same manner as described in Preparation 1-(3). The crude product thus obtained is recrystallized from benzene, whereby 21.67 g of 1-(4-acetamido-2-methoxyphenoxy)-3-(p-toluenesulfonyloxy)-n-propane are obtained as colorless prisms. Yield: 91%

M.p. 90° C.–91° C.

PREPARATION 3

A solution of 5.6 g of methanesulfonyl chloride in 10 ml of pyridine is dropwise added under ice-cooling to a solution of 9.5 g of 1-(4-acetamido-2-methoxyphenoxy)-3-hydroxy-n-propane in 90 ml of pyridine. The mixture is stirred at a temperature below 10° C. for 2 hours. The reaction mixture is poured into ice-water, and the aqueous mixture is extracted with ethyl acetate. The extract is washed with 10% hydrochloric acid and water, successively. Said extract is dried and then evaporated under reduced pressure to remove the solvent. The residue is recrystallized from a mixture of ethyl acetate and isopropyl ether, whereby 10.54 g of 1-(4-acetamido-2-methoxyphenoxy)-3-(methanesulfonyloxy)-n-propane are obtained as colorless needles. Yield: 81.3%

M.p. 90° C.–91° C.

PREPARATION 4

(1) 10 g of 4-acetamido-2-methoxyphenol, 3.5 g of 96% powdery potassium hydroxide, 10.9 g of 3-chloro-1-(tetrahydropyran-2-yl-oxy)-n-propane and 100 ml of dimethylsulfoxide are treated in the same manner as described in Preparation 1-(1). The crude product thus obtained is recrystallized from a mixture of benzene and isopropyl ether, whereby 15.55 g of 1-(4-acetamido-2-methoxyphenoxy)-3-(tetrahydropyran-2-yl-oxy)-n-propane are obtained as colorless needles. Yield: 87%

M.p. 86° C.–87° C.

(2) 13.25 g of 1-(4-acetamido-2-methoxyphenoxy)-3-(tetrahydropyran-2-yl-oxy)-n-propane are dissolved in a mixture of 60 ml of ethanol and 120 ml of water, and 0.1 ml of conc. hydrochloric acid is added thereto. The mixture is stirred at room temperature for 3 hours, and further stirred at 50° C. for 2 hours. The reaction mixture is concentrated under reduced pressure to dryness. The residue is recrystallized from acetone, whereby 9.67 g of 1-(4-acetamido-2-methoxyphenoxy)-3-hydroxy-n-propane are obtained as colorless needles. Yield: 98.6%

The physico-chemical properties of the product are identical with those of the sample obtained in Preparation 2-(2).

(3) The product obtained in paragraph (2) is treated in the same manner as described in Preparation 1-(3), whereby 1-(4-acetamido-2-methoxyphenoxy)-3-(p-toluenesulfonyloxy)-n-propane is obtained.

PREPARATION 5

(1) 5 g of 4-acetamido-2-methoxyphenol are dissolved in 30 ml of dimethylsulfoxide under nitrogen atmosphere, and 1.75 g of 96% powdery potassium hydroxide are added thereto. The mixture is stirred at 55° C. for 2 hours. Then, 2.83 g of 3-chloropropanol are added at 30° C. to the mixture, and said mixture is stirred at 55° C. for 2 hours. The reaction mixture is poured into ice-water, and the aqueous mixture is extracted with chloroform. The extract is washed with water, dried and then evaporated under reduced pressure to remove the solvent. The residue is recrystallized from acetone, whereby 1.85 g of 1-(4-(4-acetamido-2-methoxyphenoxy)-3-hydroxy-in-propane are obtained as colorless needles. The physico-chemical properties of the product are identical with those of the sample obtained in Parparation 2-(2).

(2) The product obtained in paragraph (1) is treated in the same manner as described in Preparation 1-(3), whereby 1-(4-acetamido-2-methoxyphenoxy)-3-(p-toluenesulfonyloxy)-n-propane is obtained.

PREPARATION 6

(1) 12.7 g of 4-acetamido-2-methoxyphenol, 2.95 g of powdery sodium hydroxide, 11.7 g of 4-chloro-1-(tetrahydropyran-2-yl-oxy)-n-butane and 180 ml of dimethylsulfoxide are treated in the same manner as described in Preparation 1-(1). The crude product thus obtained is recrystallized from a mixture of benzene and isopropyl ether, whereby 18.08 g of 1-(4-acetamido-2-methoxyphenoxy)-4-(tetrahydropyran-2-yl-oxy)-n-butane are obtained as colorless blades. Yield: 76.5%

M.p. 85° C.-86° C.

(2) 18 g of 1-(4-acetamido-2-methoxyphenoxy)-4-(tetrahydropyran-2-yl-oxy)-n-butane, 60 ml of ethanol, 120 ml of water and 0.1 ml of conc. hydrochloric acid are treated in the same manner as described in Preparation 1-(2). The crude product thus obtained is recrystallized from ethyl acetate, whereby 13.3 g of 1-(4-acetamido-2-methoxyphenoxy)-4-hydroxy-n-butane are obtained as colorless needles. Yield: 98.6%

M.p. 107° C.-108° C.

(3) 12.4 g of 1-(4-acetamido-2-methoxyphenoxy)-4-hydroxy-n-butane, 14.1 g of p-toluenesulfonyl chloride and 150 ml of pyridine are treated in the same manner as described in Preparation 1-(3). The crude product thus obtained is recrystallized from benzene, whereby 11.37 g of 1-(4-acetamido-2-methoxyphenoxy)-4-(p-toluenesulfonyloxy)-n-butane are obtained as colorless needles. Yield: 57%

M.p. 117° C.-118° C.

Analysis calculated for $C_{20}H_{25}NO_6S.\frac{1}{2} C_6H_6$: C, 59.98; H, 6.23; N, 3.34; S, 7.62. Found: C, 59.71; H, 6.30; N, 3.44; S, 7.41.

PREPARATION 7

(1) 3.05 g of 4-acetamido-2-methoxyphenol, 670 mg of sodium hydroxide, 3.1 g of 6-chloro-1-(tetrahydropyran-2-yl-oxy)-n-hexane and 40 ml of dimethylsulfoxide are treated in the same manner as described in Preparation 1-(1). The crude product thus obtained is recrystallized from a mixture of ethyl acetate and n-hexane, whereby 4.85 g of 1-(4-acetamido-2-methoxyphenoxy)-6-(tetrahydropyran-2-yl-oxy)-n-hexane are obtained as colorless needles. Yield: 95%

M.p. 74° C.-75.5° C.

(2) 4.88 g of 1-(4-acetamido-2-methoxyphenoxy)-6-(tetrahydropyran-2-yl-oxy)-n-hexane, 40 ml of ethanol, 80 ml of water and 0.1 ml of conc. hydrochloric acid are treated in the same manner as described in Preparation 1-(2). The crude product thus obtained is recrystallized from ethanol, whereby 2.91 g of 1-(4-acetamido-2-methoxyphenoxy)-6-hydroxy-n-hexane are obtained as colorless needles. Yield: 77.4%

IR$\nu_{max}^{Nujol}$ (cm$^{-1}$): 3270, 3150, 1660, 1140, 1030

NMR (DMSO-$d_6$)$\delta$: 9.47 (broad s, 1H, —NH—), 7.2-6.5 (m, 3H, aromatic), 4.5-3.0 (m, 5H), 3.65 (s, 3H, —OC$H_3$), 1.95 (s, 3H, C$H_3$CONH—), 2.2-1.0 (m, 8H)

Mass m/e: 281 (M+), 181 (base peak), 139

(3) 2.5 g of 1-(4-acetamido-2-methoxyphenoxy)-6-hydroxy-n-hexane, 2.03 g of p-toluenesulfonyl chloride and 50 ml of pyridine are treated in the same manner as described in Preparation 1-(3). The crude product thus obtained is recrystallized from ethyl acetate, whereby 2.49 g of 1-(4-acetamido-2-methoxyphenoxy)-6-(p-toluenesulfonyloxy)-n-hexane are obtained as colorless needles. Yield: 64%

M.p. 92° C.-93° C.

PREPARATION 8

(1) 0.5 ml of acetic acid are added under cooling to a mixture of 20 g of 4-phenylpiperazine and 70 g of ethyl acrylate, and the mixture is stirred at room temperature for 1.5 hours. Benzene is added to the reaction mixture, and said mixture is extracted with 10% hydrochloric acid. The extract is adjusted to a pH of 11 with 10% sodium hydroxide and sodium carbonate, and then extracted with benzene. The benzene extract is washed with an aqueous saturated sodium chloride solution, dried and then evaporated under reduced pressure to remove the solvent. The residue is distilled under reduced pressure, whereby 31.7 g of 1-(2-ethoxycarbonylethyl)-4-phenyl-piperazine are obtained as a colorless oil. Yield: 98%

B.p. 154° C.-155° C. (2 mmHg)

(2) 6.75 g of 1-(2-ethoxycarbonylethyl)-4-phenylpiperazine are dissolved in 100 ml of anhydrous tetrahydrofuran, and the solution is added dropwise at a temperature below 5° C. to a suspension of 1.96 g of lithium aluminum hydride in 200 ml of anhydrous tetrahydrofuran. The mixture is stirred at the same temperature for 2 hours. After decomposing an excess of lithium aluminum hydride, insoluble materials are removed by filtration. The filtrate is concentrated under reduced pressure to dryness, and the residue is recrystallized from isopropyl ether. 5.34 g of 1-(3-hydroxy-n-propyl)-4-phenyl-piperazine are thereby obtained as colorless granules. Yield: 94%

M.p. 72° C.-73° C.

(3) 10 g of 1-(3-hydroxy-n-propyl)-4-phenyl-piperazine and 5.6 g of triethylamine are dissolved in 125 ml of methylene chloride, and a solution of 6.95 g of p-toluenesulfonyl chloride in 75 ml of methylene chloride is added dropwise thereto. The mixture is refluxed for 10 hours. After cooling, the reaction mixture is washed with water, dried and then evaporated under reduced pressure to remove the solvent. The residue is distilled under reduced pressure, whereby 7.68 g of 1-(3-chloro-n-propyl)-4-phenyl-piperazine are obtained as an oil. Yield: 71%

B.p. 155° C.-158° C. (0.5 mmHg)

PREPARATION 9

(1) 5 g of 4-(2-fluorophenyl)piperazine, 13.9 g of ethyl acrylate and 0.2 ml of acetic acid are treated in the same manner as described in Preparation 8-(1), whereby 6.0 g of 1-(2-ethoxycarbonyl-ethyl)-4-(2-fluorophenyl)-piperazine are obtained as a colorless oil. Yield: 77.2%

B.P. 188° C.-190° C. (6 mm Hg)

(2) 6.0 g of 1-(2-ethoxycarbonyl-ethyl)-4-(2-fluorophenyl)-piperazine, 1.22 g of lithium aluminum hydride and 250 ml of anhydrous ether are treated in the same manner as described in Preparation 8-(2). The crude product thus obtained is recrystallized from isopropyl ether, whereby 4.65 g of 1-(3-hydroxy-n-propyl)-4-(2-fluorophenyl)-piperazine are obtained as colorless plates. Yield: 91.2%

M.P. 77° C.-79° C.

(3) 10.74 g of 1-(3-hydroxy-n-propyl)-4-(2-fluorophenyl)-piperazine, 5.92 g of triethylamine, 11.2 g of p-toluenesulfonyl chloride and 180 ml of methylene chloride are treated in the same manner as described in Preparation 8-(3). The crude product thus obtained is purified by silica gel chromatography (Solvent; 2% methanol/chloroform), whereby 11.37 g of 1-(3-chloro-n-propyl)-4-(2-fluorophenyl)-piperazine are obtained as a pale yellow oil. Yield: 98%

IR $\nu_{max}^{liq.}$ (cm$^{-1}$): 1600, 1240

NMR (CDCl$_3$)δ: 7.5–6.6 (m, 4H, aromatic), 3.63 (t, 2H, J=6.7 Hz, —CH$_2$CH$_2$Cl), 3.35–2.87 (m, 4H), 2.85–2.32 (m, 6H), 2.3–1.65 (m, 2H)

Mass m/e: 258, 256 (M+), 193 (base peak)

PREPARATION 10

(1) 8.44 g of 4-(3-methylphenyl)piperazine, 24 g of ethyl acrylate and 0.2 ml of acetic acid are treated in the same manner as described in Preparation 8-(1), whereby 11.33 g of 1-(2-ethoxycarbonylethyl)-4-(3-methylphenyl)-piperazine are obtained as a colorless oil. Yield: 85.5%

B.P. 160° C.-162° C. (0.65 mm Hg)

(2) 11.3 g of 1-(2-ethoxycarbonyl-ethyl)-4-(3-methylphenyl)-piperazine, 3.12 g of lithium aluminum hydride and 300 ml of anhydrous tetrahydrofuran are treated in the same manner as described in Preparation 8-(2). The crude product thus obtained is recrystallized from isopropyl ether, whereby 8.61 g of 1-(3-hydroxy-n-propyl)-4-(3-methylphenyl)piperazine are obtained as colorless blades. Yield: 90%

M.P. 78° C.-79° C.

(3) 5 g of 1-(3-hydroxy-n-propyl)-4-(3-methylphenyl)piperazine, 2.83 g of triethylamine, 5.35 g of p-toluenesulfonyl chloride and 90 ml of methylene chloride are treated in the same manner as described in Preparation 8-(3). The crude product thus obtained is purified by silica gel chromatography (Solvent; 2% methanol/chloroform), whereby 4.2 g of 1-(3-chloro-n-propyl)-4-(3-methylphenyl)-piperazine are obtained as a pale yellow oil. Yield: 85%

IR $\nu_{max}^{liq.}$ (cm$^{-1}$): 1605, 1250

NMR (CDCl$_3$) δ: 7.3–6.5 (m, 4H, aromatic), 3.61 (t, 2H, J=6.2 Hz, —CH$_2$CH$_2$Cl), 3.4–3.0 (m, 4H), 2.8–2.3 (m, 6H), 2.30 (s, 3H, —CH$_3$), 2.2–1.6 (m, 2H)

Mass m/e: 254, 252 (M+), 189 (base peak)

PREPARATION 11

(1) 11.55 g of 4-(3-chlorophenyl)piperazine, 29.5 g of ethyl acrylate and 0.3 ml of acetic acid are treated in the same manner as described in Preparation 8-(1), whereby 16.12 g of 1-(2-ethoxycarbonylethyl)-4-(3-chlorophenyl)-piperazine are obtained as a colorless oil. Yield: 92.5%

B.p. 160° C.-162° C. (0.15 mm Hg)

(2) 16 g of 1-(2-ethoxycarbonyl-ethyl)-4-(3-chlorophenyl)-piperazine, 4.1 g of lithium aluminum hydride and 400 ml of anhydrous tetrahydrofuran are treated in the same manner as described in Preparation 8-(2). The crude product thus obtained is recrystallized from isopropyl ether, whereby 12.4 g of 1-(3-hydroxy-n-propyl)-4-(3-chlorophenyl)-piperazine are obtained as colorless needles. Yield: 91%

M.p. 86° C.-87° C.

(3) 5 g of 1-(3-hydroxy-n-propyl)-4-(3-chlorophenyl)-piperazine, 2.58 g of triethylamine, 4.86 g of p-toluenesulfonyl chloride and 90 ml of methylene chloride are treated in the same manner as described in Preparation 8-(3). The crude product thus obtained is purified by silica gel chromatography (Solvent; 2% methanol/chloroform), whereby 3.73 g of 1-(3-chloro-n-propyl)-4-(3-chlorophenyl)-piperazine are obtained as a pale yellow oil. Yield: 87%

IR $\nu_{max}^{liq.}$ (cm$^{-1}$): 1595, 1245

NMR (CDCl$_3$) δ: 7.4–6.6 (m, 4H, aromatic), 3.62 (t, 2H, J=6.3 Hz, —CH$_2$CH$_2$Cl), 3.4–3.0 (m, 4H), 2.8–2.3 (m, 6H), 2.3–1.7 (m, 2H)

Mass m/e: 276, 274, 272 (M$^{30}$), 211, 209 (base peak)

PREPARATION 12

(1) 10 g of 4-(3-fluorophenyl)piperazine, 28 g of ethyl acrylate and 0.2 g of acetic acid are treated in the same manner as described in Preparation 8-(1), whereby 14.27 g of 1-(2-ethoxycarbonylethyl)-4-(3-fluorophenyl)-piperazine are obtained as a colorless oil. Yield: 91.6%

B.p. 148° C.-150° C. (0.25 mm Hg)

(2) 14.2 g of 1-(2-ethoxycarbonylethyl)-4-(3-fluorophenyl)-piperazine, 3.79 g of lithium aluminum hydride and 400 ml of anhydrous tetrahydrofuran are treated in the same manner as described in Prepration 8-(2). The crude product thus obtained is recrystallized from isopropyl ether, whereby 10.84 g of 1-(3-hydroxy-n-propyl)-4-(3-fluorophenyl)-piperazine are obtained as colorless needles. Yield: 90%

M.P. 74° C.-75° C.

(3) 5 g of 1-(3-hydroxy-n-propyl)-4-(3-fluorophenyl)-piperazine, 2.79 g of triethylamine, 5.37 g of p-toluenesulfonyl chloride and 90 ml of methylene chloride are treated in the same manner as described in Preparation 8-(3). The crude product thus obtained is purified by silica gel chromatography (Solvent; 2% methanol/chloroform), whereby 4.3 g of 1-(3-chloro-n-propyl)-4-(3-fluorophenyl)-piperazine are obtained as a pale yellow oil. Yield: 87%

IR $\nu_{max}^{liq.}$ (cm$^{-1}$): 1615

NMR (CDCl$_3$) δ: 7.45–6.3 (m, 4H, aromatic), 3.61 (t, 2H, J=6.4 Hz, —CH$_2$CH$_2$Cl), 3.4–3.0 (m, 4H), 2.8–2.3 (m, 6H), 2.2–1.6 (m, 2H)

Mass m/e: 258, 256 (M+), 193 (base peak)

PREPARATION 13

(1) 5.0 g of 4-phenylpiperazine are dissolved in 50 ml of ethanol, and 3.92 g of ethylene chlorohydrin and 6.4 g of potassium carbonate are added thereto. The mixture is refluxed for 10 hours. Then, the mixture is evaporated under reduced pressure to remove ehtanol. Water is added to the residue, and the aqueous mixture is extracted with methylene chloride. The extract is washed with water, dried and then evaporated under reduced pressure. The residue is recrystallized from isopropyl ether, whereby 5.55 g of 1-(2-hydroxyethyl)-4-phenyl-piperazine are obtained as colorless needles. Yield: 87.5%

M.P. 81° C.–82.5° C.

(2) 5 g of 1-(2-hydroxyethyl)-4-phenyl-piperazine, 3.64 g of triethylamine, 6.95 g of p-toluenesulfonyl chloride and 80 ml of methylene chloride are treated in the same manner as described in Preparation 8-(3). The crude product thus obtained is purified by silica gel chromatography (Solvent; 2% methanol/chloroform), whereby 2.8 g of 1-(2-chloroethyl)-4-phenyl-piperazine are obtained. Yield: 51.7%

M.p. 59° C.–60° C. (colorless needles, recrystallized from n-hexane)

What we claim is:

1. A method of reducing increased intracranial pressure in a warm-blooded animal which comprises administering to a warm-blooded animal in need of such reduction of intracranial pressure a therapeutically effective amount of a piperazine compound of the formula:

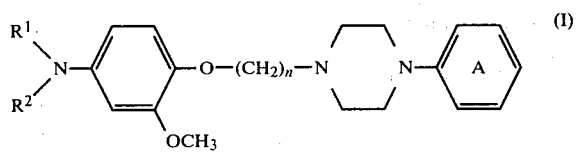

wherein $R^1$ is hydrogen, alkyl ($C_{1-8}$), alkyl ($C_{1-4}$)-sulfonyl or an acyl group of the formula: $R^3CO$— (wherein $R^3$ is hydrogen, alkyl ($C_{1-7}$), halogenoalkyl ($C_{1-4}$), alkoxy ($C_{1-4}$)-carbonyl-alkyl ($C_{1-4}$), cycloalkyl ($C_{3-6}$), alkenyl ($C_{2-5}$), alkoxy ($C_{1-4}$), amino, alkyl ($C_{1-4}$)-amino or anilino), $R^2$ is hydrogen, alkyl ($C_{1-4}$), alkoxy ($C_{1-4}$)-carbonyl-alkyl ($C_{1-4}$), carboxy-alkyl ($C_{1-4}$), alkenyl ($C_{2-5}$) or alkyl ($C_{1-4}$)-sulfonyl, or $R^1$ and $R^2$ are combined together to form succinyl group, Ring A is phenyl, alkyl ($C_{1-4}$)-phenyl or halogenophenyl, and n is an integer of 2 to 6, or a pharmaceutically acceptable acid addition salt thereof.

2. The method of claim 1, in which $R^1$ is hydrogen, alkyl ($C_{1-8}$), alkyl ($C_{1-4}$)-sulfonyl, formyl, alkyl ($C_{1-7}$)-carbonyl, cycloalkyl ($C_{3-6}$)-carbonyl, alkenyl ($C_{2-5}$)-carbonyl, alkoxy ($C_{1-4}$)-carbonyl or carbamoyl, $R^2$ is hydrogen, alkyl ($C_{1-4}$) or carboxy-alkyl ($C_{1-4}$), and n is an integer of 2 to 4.

3. The method of claim 1, in which $R^1$ is hydrogen, alkyl ($C_{1-8}$), formyl, alkyl ($C_{1-7}$)-carbonyl, cycloalkyl ($C_{3-6}$)-carbonyl, alkenyl ($C_{2-5}$)-carbonyl or alkoxy ($C_{1-4}$)-carbonyl, $R^2$ is hydrogen, alkyl ($C_{1-4}$) or carboxy-alkyl ($C_{1-4}$), and n is 3 or 4.

4. The method of claim 2, in which Ring A is phenyl, methylphenyl, chlorophenyl or fluorophenyl.

5. The method of claim 3, in which Ring A is phenyl, methylphenyl, chlorophenyl, fluorophenyl.

6. The method of claim 4, in which $R^1$ is hydrogen, methyl, ethyl, formyl, acetyl, isopropylcarbonyl, t-butylcarbonyl, cyclopropylcarbonyl, cyclohexylcarbonyl, (2-methyl-1-propenyl)-carbonyl, ethoxycarbonyl or t-butoxycarbonyl, $R^2$ is hydrogen, methyl or 1-carboxyethyl, and Ring A is phenyl, 3-methylphenyl, 2-chlorophenyl, 3-chlorophenyl, 2-fluorophenyl or 3-fluorophenyl.

7. The method of claim 5, in which $R^1$ is hydrogen, methyl, ethyl, formyl, acetyl, isopropylcarbonyl, t-butylcarbonyl, cyclopropylcarbonyl, cyclohexylcarbonyl, ethoxycarbonyl or t-butoxycarbonyl, $R^2$ is hydrogen, methyl or 1-carboxyethyl, and Ring A is phenyl, 3-methylphenyl, 2-fluorophenyl or 3-fluorophenyl.

8. The method of claim 5, in which $R^1$ is methyl, ethyl, acetyl or t-butoxycarbonyl, $R^2$ is hydrogen or methyl, Ring A is phenyl, 3-methylphenyl, 2-fluorophenyl or 3-fluorophenyl, and n is 3.

9. The method of claim 8, which is 1-[3-(4-acetamido-2-methoxyphenoxy)-n-propyl]-4-phenyl-piperazine or a pharmaceutically acceptable acid addition salt thereof.

10. The method of claim 8, which is 1-[3-(4-acetamido-2-methoxyphenoxy)-n-propyl]-4-(3-methylphenyl)-piperazine or a pharmaceutically acceptable acid addition salt thereof.

11. The method of claim 8, which is 1-[3-(4-acetamido-2-methoxyphenoxy)-n-propyl]-4-(3-fluorophenyl)-piperazine or a pharmaceutically acceptable acid addition salt thereof.

12. The method of claim 8, which is 1-[3-(4-acetamido-2-methoxyphenoxy)-n-propyl]-4-(2-fluorophenyl)-piperazine or a pharmaceutically acceptable acid addition salt thereof.

13. The method of claim 8, which is 1-[3-(4-ethylamino-2-methoxyphenoxy)-n-propyl]-4-phenyl-piperazine or a pharmaceutically acceptable acid addition salt thereof.

14. The method of claim 8, which is 1-[3-(4-t-butoxycarbonylamino-2-methoxyphenoxy)-n-propyl]-4-phenyl-piperazine or a pharmaceutically acceptable acid addition salt thereof.

15. The method of claim 8, which is 1-[3-(4-dimethylamino-2-methoxyphenoxy)-n-propyl]-4-phenyl-piperazine or a pharmaceutically acceptable acid addition salt thereof.

16. The method according to claim 1, wherein the piperazine compound (I) or a pharmaceutically acceptable acid addition salt thereof is administered at a daily dose of 0.05 to 50 mg (in terms of free base) per kilogram of body weight.

17. The method according to claim 1, wherein the piperazine compound (I) or a pharmaceutically acceptable acid addition salt thereof is administered at a daily dose of 0.1 to 10 mg (in terms of free base) per kilogram of body weight.

18. The method of claim 1 wherein $R^1$ is methyl, ethyl, formyl, acetyl, isopropylcarbonyl, t-butylcarbonyl, cyclopropylcarbonyl, cyclohexylcarbonyl, (2-methyl-1-propenyl)-carbonyl, ethoxycarbonyl or t-butoxycarbonyl, $R^2$ is hydrogen or methyl, Ring A is phenyl, 2-methylphenyl, 3-methylphenyl, 4-methylphenyl, 2-chlorophenyl, 3-chlorophenyl, 2-fluorophenyl or 3-fluorophenyl, and n is 3 or 4.

19. The method according to claim 18 wherein $R^1$ is ethyl, formyl, acetyl, isopropylcarbonyl, (2-methyl-1-propenyl)-carbonyl, ethoxycarbonyl, or t-butoxycarbonyl, $R^2$ is hydrogen, Ring A is phenyl, 3-methylphenyl, 2-fluorophenyl or 3-fluorophenyl, and n is 3 or 4.

* * * * *

UNITED STATES PATENT AND TRADEMARK OFFICE
CERTIFICATE OF CORRECTION

PATENT NO. : 4,413,006

DATED : November 1, 1983

INVENTOR(S) : KANNO, et al

It is certified that error appears in the above-identified patent and that said Letters Patent are hereby corrected as shown below:

```
Column 1, line 24, change "carbon-alkyl" to
--carbonyl-alkyl--.
Column 1, line 30, correct "halogeno".
Column 1, line 33, correct "complication".
Column 2, line 24, correct "suspensions".
Column 2, line 31, correct "methyl".
Column 2, line 37, after "propenyl)" insert --,--.
Column 5, line 60, change "R³" to --R⁴--.
Column 7, line 37, change "the" first occurrence to --The--.
Column 7, line 40, change "of" second occurrence to --or--.
Column 8, line 23, change "of" to --or--.
Column 8, line 24, correct "compound".
Column 8, line 57, change "of" first occurrence to --or--.

Column 13, line 55, insert --:-- after "activity".
Column 14, line 62, insert --:-- after "activity".
Column 17, line 57, change "68.4" to --6.84--.
Column 17, line 58, correct "-OCH₂CH₂-".
Column 22, line 42, correct "4-phenylpiperazine".
```

UNITED STATES PATENT AND TRADEMARK OFFICE
CERTIFICATE OF CORRECTION

PATENT NO. : 4,413,006

DATED : November 1, 1983

INVENTOR(S) : KANNO, et al

It is certified that error appears in the above-identified patent and that said Letters Patent is hereby corrected as shown below:

Column 24, lines 1-5, change "-CO-CHO" to --CH(-H)--, and change "-CO-" to -- -CO- --.

Column 24, line 25, change "(M-)" to --(M+)--.
Column 24, line 43, change "3.5" to --3.4--.
Column 31, line 57, correct "-OCH₃)".
Column 35, line 19, after "hydroxy-" change "in-propane" to --n-propane--.
Column 35, lines 21-22, correct "preparation".
Column 38, line 27, change "M30" to --M+--.
Column 38, line 65, correct "ethanol".

Signed and Sealed this

Twelfth Day of February 1985

[SEAL]

Attest:

DONALD J. QUIGG

Attesting Officer — Acting Commissioner of Patents and Trademarks